(12) United States Patent
Mishra et al.

(10) Patent No.: US 9,351,999 B2
(45) Date of Patent: May 31, 2016

(54) USE OF PLATELET RICH PLASMA COMPOSITION IN THE TREATMENT OF CARDIAC CONDUCTION ABNORMALITIES

(71) Applicant: BioParadox, LLC, Menlo Park, CA (US)

(72) Inventors: Allan Kumar Mishra, Menlo Park, CA (US); Todd Jeffrey Brinton, Menlo Park, CA (US)

(*) Notice: Subject to any disclaimer, the term of this patent is extended or adjusted under 35 U.S.C. 154(b) by 0 days.

(21) Appl. No.: 14/473,107

(22) Filed: Aug. 29, 2014

(65) Prior Publication Data

US 2015/0037431 A1 Feb. 5, 2015

Related U.S. Application Data

(62) Division of application No. 12/575,314, filed on Oct. 7, 2009, now abandoned.

(60) Provisional application No. 61/103,464, filed on Oct. 7, 2008.

(51) Int. Cl.

| | | |
|---|---|---|
| A61K 35/16 | (2015.01) | |
| A61N 1/36 | (2006.01) | |
| A61N 1/362 | (2006.01) | |
| A61B 5/0402 | (2006.01) | |
| A61B 5/00 | (2006.01) | |
| A61K 45/06 | (2006.01) | |
| A61M 15/00 | (2006.01) | |
| A61M 16/14 | (2006.01) | |

(52) U.S. Cl.
CPC .............. *A61K 35/16* (2013.01); *A61B 5/0402* (2013.01); *A61B 5/4848* (2013.01); *A61K 45/06* (2013.01); *A61M 15/009* (2013.01); *A61M 16/14* (2013.01); *A61N 1/362* (2013.01); *A61N 1/36114* (2013.01); *A61M 2202/0007* (2013.01); *A61M 2202/0415* (2013.01); *A61M 2202/0427* (2013.01)

(58) Field of Classification Search
None
See application file for complete search history.

(56) References Cited

U.S. PATENT DOCUMENTS

| | | |
|---|---|---|
| 4,081,331 A | 3/1978 | Weiss |
| 4,414,108 A | 11/1983 | Ito et al. |
| 4,663,289 A | 5/1987 | Veech |
| 4,931,395 A | 6/1990 | Griffin |
| 4,957,742 A | 9/1990 | Knighton |
| 5,079,236 A | 1/1992 | Drizen et al. |
| 5,124,316 A | 6/1992 | Antoniades et al. |
| 5,147,776 A | 9/1992 | Koerner, Jr. |
| 5,165,938 A | 11/1992 | Knighton |
| 5,178,883 A | 1/1993 | Knighton |
| 5,209,724 A | 5/1993 | Dhaliwal et al. |
| 5,269,290 A | 12/1993 | Barrett et al. |
| 5,313,953 A | 5/1994 | Yomtov et al. |
| 5,336,387 A | 8/1994 | Egen et al. |
| 5,385,937 A | 1/1995 | Stamler et al. |
| 5,403,272 A | 4/1995 | Deniega et al. |
| 5,449,688 A | 9/1995 | Wahl et al. |
| 5,474,891 A | 12/1995 | Murphy |
| 5,494,590 A | 2/1996 | Smith et al. |
| 5,510,102 A | 4/1996 | Cochrum |
| 5,578,460 A | 11/1996 | Ebersole et al. |
| 5,578,565 A | 11/1996 | Chao et al. |
| 5,585,007 A | 12/1996 | Antanavich et al. |
| 5,599,558 A | 2/1997 | Gordinier et al. |
| 5,614,204 A | 3/1997 | Cochrum |
| 5,643,786 A | 7/1997 | Cohen et al. |
| 5,676,849 A | 10/1997 | Sammons et al. |
| 5,733,545 A | 3/1998 | Hood |
| 5,773,033 A | 6/1998 | Cochrum et al. |
| 5,785,869 A | 7/1998 | Martinson et al. |
| 5,788,662 A | 8/1998 | Antanavich et al. |
| 5,834,418 A | 11/1998 | Brazeau et al. |
| 5,905,142 A | 5/1999 | Murray |
| 5,916,743 A | 6/1999 | Lake et al. |
| 5,928,214 A | 7/1999 | Rubinstein et al. |
| 5,935,850 A | 8/1999 | Clark et al. |
| 5,993,804 A | 11/1999 | Read et al. |
| 6,063,297 A | 5/2000 | Antanavich et al. |
| 6,098,631 A | 8/2000 | Holoshitz et al. |
| 6,102,926 A | 8/2000 | Tartaglia et al. |

(Continued)

FOREIGN PATENT DOCUMENTS

| | | |
|---|---|---|
| EP | 0142339 | 5/1985 |
| EP | 0417818 | 3/1991 |

(Continued)

OTHER PUBLICATIONS

Cohen, et al. "Wound Care and Wound Healing," in Principles of Surgery, Chapter 8 (Seymore, et al. eds.) pp. 263-295, New York, 1999.

(Continued)

*Primary Examiner* — Kade Ariani

(74) *Attorney, Agent, or Firm* — Knobbe, Martens, Olson & Bear, LLP

(57) ABSTRACT

Methods and kits for treating a cardiac arrhythmia using a platelet rich plasma (PRP) composition are provided. Any type of arrhythmia may be treated using the PRP composition. The PRP composition may comprise PRP developed using blood collected from a patient suffering the cardiac arrhythmia. The PRP composition may be buffered to a physiological pH and may include one or more anti-arrhythmic agents, anti-coagulants, or other drugs. The PRP composition may be delivered using a nebulizer, minimally invasively, or surgically.

13 Claims, 4 Drawing Sheets

(56) References Cited

U.S. PATENT DOCUMENTS

| | | |
|---|---|---|
| 6,120,520 A | 9/2000 | Saadat et al. |
| 6,132,396 A | 10/2000 | Antanavich et al. |
| 6,183,442 B1 | 2/2001 | Athanasiou et al. |
| 6,210,976 B1 | 4/2001 | Sabbadini |
| 6,214,338 B1 | 4/2001 | Antanavich et al. |
| 6,242,594 B1 | 6/2001 | Kelly |
| 6,280,473 B1 | 8/2001 | Lemperle et al. |
| 6,315,992 B1 | 11/2001 | Noh et al. |
| 6,322,785 B1 | 11/2001 | Landesberg et al. |
| 6,432,119 B1 | 8/2002 | Saadat |
| 6,444,228 B1 | 9/2002 | Baugh et al. |
| 6,447,443 B1 | 9/2002 | Keogh et al. |
| 6,454,804 B1 | 9/2002 | Ferree |
| 6,596,179 B2 | 7/2003 | Giesler et al. |
| 6,712,851 B1 | 3/2004 | Lemperle et al. |
| 6,811,777 B2 | 11/2004 | Mishra |
| 6,837,848 B2 | 1/2005 | Bonner et al. |
| 6,905,612 B2 | 6/2005 | Dorian et al. |
| 6,942,639 B2 | 9/2005 | Baugh et al. |
| 6,942,880 B1 | 9/2005 | Dolecek et al. |
| 7,169,547 B2 | 1/2007 | Rubinstein et al. |
| 7,179,249 B2 | 2/2007 | Steward et al. |
| 7,211,191 B2 | 5/2007 | Coelho et al. |
| 7,252,758 B2 | 8/2007 | Dolecek et al. |
| 7,314,617 B2 | 1/2008 | Mishra |
| 7,462,268 B2 | 12/2008 | Mishra |
| 7,608,258 B2 | 10/2009 | Mishra |
| 7,708,152 B2 | 5/2010 | Dorian et al. |
| 8,142,993 B1 | 3/2012 | Mishra |
| 8,163,277 B2 | 4/2012 | Mishra |
| 8,440,459 B2 | 5/2013 | Mishra |
| 8,444,969 B2 | 5/2013 | Mishra |
| 2001/0031978 A1 | 10/2001 | Kipke et al. |
| 2002/0004038 A1 | 1/2002 | Baugh et al. |
| 2002/0006437 A1 | 1/2002 | Grooms et al. |
| 2002/0032155 A1 | 3/2002 | Ferree |
| 2002/0058030 A1 | 5/2002 | Monroy et al. |
| 2002/0082220 A1 | 6/2002 | Hoemann et al. |
| 2002/0147611 A1 | 10/2002 | Greene et al. |
| 2003/0116512 A1 | 6/2003 | Delbert Antwiler et al. |
| 2003/0152639 A1 | 8/2003 | Britton et al. |
| 2003/0175248 A1 | 9/2003 | Uhr |
| 2003/0185812 A1 | 10/2003 | Ferree |
| 2003/0191005 A1 | 10/2003 | Coelho et al. |
| 2003/0192554 A1 | 10/2003 | Ferree |
| 2003/0205538 A1 | 11/2003 | Dorian et al. |
| 2003/0233064 A1 | 12/2003 | Arm et al. |
| 2003/0236573 A1 | 12/2003 | Evans et al. |
| 2004/0091459 A1 | 5/2004 | Nimni |
| 2004/0126885 A1 | 7/2004 | Cines et al. |
| 2004/0131583 A1 | 7/2004 | Barritault et al. |
| 2004/0182795 A1 | 9/2004 | Dorian et al. |
| 2004/0220101 A1 | 11/2004 | Ferree |
| 2004/0220102 A1 | 11/2004 | Ferree |
| 2004/0244806 A1 | 12/2004 | Ferree |
| 2005/0043738 A1 | 2/2005 | Ryan |
| 2005/0064042 A1 | 3/2005 | Vunjak-Novakovic et al. |
| 2005/0107323 A1 | 5/2005 | Donahue et al. |
| 2005/0186193 A1 | 8/2005 | Mishra |
| 2005/0209081 A1 | 9/2005 | Baugh et al. |
| 2005/0209564 A1 | 9/2005 | Bonner et al. |
| 2006/0029578 A1 | 2/2006 | Hoemann et al. |
| 2006/0041243 A1 | 2/2006 | Nayak et al. |
| 2006/0068369 A1 | 3/2006 | Coelho et al. |
| 2006/0127382 A1 | 6/2006 | Mishra |
| 2006/0235306 A1 | 10/2006 | Cotter et al. |
| 2007/0014784 A1 | 1/2007 | Nayak et al. |
| 2007/0020735 A1 | 1/2007 | Chen et al. |
| 2007/0037737 A1 | 2/2007 | Hoemann et al. |
| 2007/0042016 A1 | 2/2007 | Nayak et al. |
| 2007/0087061 A1 | 4/2007 | Drake et al. |
| 2007/0110737 A1 | 5/2007 | Mishra |
| 2007/0122906 A1 | 5/2007 | Mishra |
| 2007/0172472 A1 | 7/2007 | Nayak |
| 2007/0179424 A1 | 8/2007 | Rubinstein et al. |
| 2007/0202093 A1 | 8/2007 | Brooks et al. |
| 2007/0264245 A1 | 11/2007 | Mishra |
| 2007/0269887 A1 | 11/2007 | Coelho et al. |
| 2008/0045964 A1 | 2/2008 | Mishra |
| 2008/0069777 A1 | 3/2008 | Cohen et al. |
| 2008/0081367 A1 | 4/2008 | Sowemimo-Coker et al. |
| 2008/0089867 A1 | 4/2008 | Fernandes et al. |
| 2008/0248081 A1 | 10/2008 | Mishra |
| 2008/0248082 A1 | 10/2008 | Mishra |
| 2008/0248083 A1 | 10/2008 | Mishra |
| 2008/0248084 A1 | 10/2008 | Mishra |
| 2008/0248085 A1 | 10/2008 | Mishra |
| 2008/0254093 A1 | 10/2008 | Mishra |
| 2008/0255471 A1 | 10/2008 | Naghavi et al. |
| 2009/0005733 A1 | 1/2009 | Chiu et al. |
| 2009/0053208 A1 | 2/2009 | Nayak |
| 2009/0092679 A1 | 4/2009 | Mishra |
| 2009/0227952 A1 | 9/2009 | Blakstvedt et al. |
| 2009/0254104 A1 | 10/2009 | Murray |
| 2010/0112081 A1 | 5/2010 | Mishra |
| 2010/0140182 A1 | 6/2010 | Chapman et al. |
| 2010/0150892 A1 | 6/2010 | Han |
| 2010/0183561 A1 | 7/2010 | Sakthivel et al. |
| 2010/0196497 A1 | 8/2010 | Lim et al. |
| 2010/0233282 A1 | 9/2010 | Mishra |
| 2013/0177623 A1 | 7/2013 | Bowlin et al. |
| 2013/0197468 A1 | 8/2013 | Schwartzman et al. |

FOREIGN PATENT DOCUMENTS

| | | |
|---|---|---|
| EP | 2258379 | 12/2010 |
| JP | 5-500516 | 2/1993 |
| WO | WO 91/04035 | 4/1991 |
| WO | WO 00/01427 | 1/2000 |
| WO | WO 00/12018 | 3/2000 |
| WO | WO 00/54661 | 9/2000 |
| WO | WO 01/43756 A2 | 6/2001 |
| WO | WO 03/015800 | 2/2003 |
| WO | WO 03/090839 A1 | 11/2003 |
| WO | WO 2004/022078 | 3/2004 |
| WO | WO 2005/065242 | 7/2005 |
| WO | WO 2007/112135 | 10/2007 |

OTHER PUBLICATIONS

Durukan, et al. "Acute Ischemic Stroke: Overview of Major Experimental Rodent Models, Pathophysiology, and Therapy of Focal Cerebral Ischemia," Pharmacology, Biochemistry and Behavoir, 87:179-197, 2007.

Fylling, et al. "Multi-Center Clinical Review: Using Autologous Platelet Gel for the Treatment of Diabetic Plantar Wounds," Diabetes, 50 (Supplement 2), A227 (Jun. 2001).

Hinkel, "The Effect of Irradiation Upon the Composition and Vascularity of Growing Bones," A.J. Roentgenol and Radium Therap. 50 (4): 516-526 (1943). (Abstract only.).

Marx, et al. "Platelet-Rich Plasma, Growth Factor Enhancement for Bone Grafts," Oral Surgery Oral Medicine Oral Pathology, vol. 85, No. 6, pp. 638-646, Jun. 1998.

Neisius et al., "Renal Oncocytoma: Diagnostic and Therapeutical Consequences," Urologe Ausgabe A., 32(5):415-419, 1993. (Abstract only.).

Ohman et al. "Cardiac Troponin T Levels for Risk Stratification in Acute Myocardial Ischemia," The New England Journal of Medicine, vol. 335, No. 18, pp. 1333-1341, Oct. 31, 1996.

Playford, et al. "Combined Effect of Coenzyme Q10 and Fenofibrate on Forearm Microcirculatory Function in Type II Diabetes," Artherosclerosis, 168:169-179, 2003.

Vasconcelos et al., "Quality of Platelet Concentrates Derived by Platelet Rich Plasma, Buffy Coat and Apheresis," Transfusion and Apheresis Science, vol. 29, No. 1, pp. 13-16, 2003.

Website download from Medtronic, "Magellan" System Features and Benefits, 3 pages, 2004.

Arnar et al., Am J Physiol. Heart Circ. Physiol., 2002, vol. 282, p. H1189-H1196.

Asanuma, et al., The Hydrogen Ion Concentration (pH) in Blood Samples With K2EDTA and K3EDTA Affects Mean Corpuscular Volume Values in Hemodialysis Patients, Laboratory Hematology, 2000, vol. 6, pp. 67-72.

(56) References Cited

OTHER PUBLICATIONS

Aster et al., "The Anticoagulants of Choice for Platelet Transfusions", Transfusion 6 (1) : 32-38 (1966).
Atherton, "Acid-base balance: maintenance of plasma pH", Anaesthesia and Intensive Care Medicine, pp. 419-422 (2003).
Boldt et al. "Acute platelet-rich plasmapheresis for cardiac surgery" Journal of Cardiothoracic and Vascular Anesthesia, Saunders, Philadelphia, PA, U.S., vol. 9, No. 1, Feb. 1, 1995, pp. 79-88, XP005227129, ISSN: 1053-0770, LNKD-DOI:10.1016/S1053-0770(05)80061-8.
Boost demineralizedbonematrix, featuring Autologous Growth Factor, Brochure, Cell Factor Technologies, Inc., 2004, pp. 6 pages.
CD15 MicroBeads, Miltenyi Biotec Inc., downloaded from www.miltenyibiotec.com, pp. 4.
Cell Factor Technologies, Inc., Brochure for GPS II Platelet Concentrate System, 10 pages, 2004.
Chen, et al., PMA-activated Neutrophils Decrease Pulmonary Endothelial Ectoenzyme Activities in Perfused Rabbit Lungs, American Journal of Physiology, Dec. 1992, vol. 263, Issue 6, pp. L650-L656.
Colditz, et al., Neutrophil Accumulation and Plasma Leakage Induced In vivo by Neutrophil-Activating Peptide-1, Journal of Leukocyte Biology, 1990, vol. 48, pp. 129-137.
Coller, et al. "The pH Dependence of Quantitative Ristocetin-Induced Platelet Aggregation: Theoretical and Practical Implications—A New Device for Maintenance of Platelet-Rich Plasma pH," Blood, vol. 47, No. 5, pp. 841-854, May 1976.
Cotter et al., "A Novel Method for Isolation of Neutrophils from Murine Blood Using Negative Immunomagnetic Separation," The American Journal of Pathology, vol. 159, pp. 473-481, 2001.
Cupo et al., "Acute left ventricular dysfunction of severe scorpion envenomation is related to myocardial perfusion disturbance," International J. Cardiology., vol. 116(1), pp. 98-106 (2007), abstract only.
DePuy AcroMed, Inc. Brochure for Symphony Platelet Concentrate System, 10 pages, 2001.
Douketis et al., The Perioperative Management of Antithrombotic Therapy, Chest 133(6):299-339S, Jun. 2008, Supplement.
Edwards et al., "Autologous Blood Injections for Refractory Lateral Epicondylitis," The Journal of Hand Surgery, vol. 28A, No. 2, pp. 272-278, Mar. 2003.
Eppley et al. "Platelet Quantification and Growth Factor Analysis from Platelet-Rich Plasma: Implications for Wound Healing," Plastic and Reconstructive Surgery, pp. 1502-1508, vol. 114, No. 6, Nov. 2004.
Esa et al., "Immunological Heterogeneity of Human Monocyte Subsets Prepared by Counterflow Centrifugation Elutriation," Immunology, vol. 59, pp. 95-99, 1986.
Extended European Search Report issued in European Patent Application No. 09819913.6, on May 10, 2013.
Farrugia et al., "Red cell and platelet concentrates from blood collected into half-strength citrate anticoagulant: improved maintenance of red cell 2,3-diphosphoglycerate in half-citrate red cells" Vox Sanguinis 63 (1) : 31-38 (1992), abstract only.
Feuerstein et al. "Congestive Heart Failure and Genomic Medicine: A Look into the 21st Century," Cardiovascular Drugs and Therapy, vol. 11, No. 6, pp. 713-717, 1997.
Fijnheer et al., "Platelet activation during preparation of platelet concentrates: a comparison of the platelet-rich plasma and the buffy coat methods," Transfusion, vol. 30(7), pp. 634-638 (1990).
Floryan et al., "Home Study Program: Intraoperative Use of Autologous Platelet-Rich and Platelet-Poor Plasma for Orthopedic Surgery Patients," Aorn Journal, vol. 80, No. 4, pp. 667-678, Oct. 2004.
Gargoyle, 2003, "Chapter 12. Blood", pp. 1-5; Published on the Web—on May 15, 2003 (at http://gargoyle.arcadia.edu/biology/bi327/chapt12.P D F).
Gawaz et al. "Platelet Function in Acute Myocardial Infarction Treated with Direct Angioplasty," Circulation, vol. 93, pp. 229-237, 1996 with "Methods, Specimen Collection, Methods, Platelet Aggregation in Vitro, Discussion, Platelet Adhesion to Endothelium in AMI," downloaded from http://circ.ahajournals.org/cgi/content/full/93/2/229 on Dec. 2, 2009.
Gehring et al., "Preparation of autologous platelets for the opthalmologic treatment of macular holes", Transfusion 39: 144-148 (1999).
Gibson et al., "Citrate-Phosphate-Dextrose Solution for Preservation of Human Blood", Transfusion 1 (5) : 280-287 (1961).
Giordano, et al., "Autologous platelet-rich plasma in cardiac surgery: Effect on intraoperative and postoperative transfusion requirements" Journal of Cardiothoracic Anesthesia , XP026263096, ISSN: 0888-6296, LNKD-DOI:10.1016/0888-6296(89)90129-4., Journal of Cardiothoracic Anesthesia, Jun. 1, 1989, vol. 3, Issue 3, pp. 367.
Gruber et al., "Platelets Stimulate Proliferation of Bone Cells: Involvement of Platelet-Derived Growth Factor, Microparticles and Membranes", Clin. Oral Impl. Res, vol. 13, pp. 529-535, 2002.
Guidance for Industry: Biological Product Deviation, Reporting for Blood and Plasma Establishments [online]. Food and Drug Administration, Oct. 2006 [retrieved on Aug. 1, 2013]. Retrieved from the Internet: (URL:http://www.fda.gov/downloads/BiologicsBloodVaccines/GuidanceComplianceRegulatoryInformation/Guidances/Blood/UCM062918.pdf).
Harvest Technologies GmbH Brochure for SmartPReP 2, 2002.
http://www.medicinenet.com/connective_tissue disease/article.htm, accessed Jun. 13, 2012. Connective Tissue Disease, pp. 1-3.
http://www.siumed.edu/-dking2/intro/ct.htm#ordinspecial, accessed Jun. 13, 2012. Histological definition of connective tissue from SIU School of Medicine, pp. 1-18.
Iba et al. "Angiogenesis by implantation of peripheral blood mononuclear cells and platelets into ischemic limbs", Circulation, 2002, vol. 106, pp. 2019-2025.
International Search Report and Written Opinion in PCT/US09/59897, dated Dec. 18, 2009.
Knebel et al., "Heart Failure: State of the Art Treatment and Options," Clinical Nephrology, vol. 60, Suppl. 1, pp. S59-S66 (2003).
Kurita et al., "Enhanced Vascularization by Controlled Release of Platelet-Rich Plasma Impregnated in Biodegradable Gelatin Hydrogel", Annals of Thoracic Surgery 92 : 837-844 (2011).
Lee et al., "Cardiac Arrhythmia 2-Catheter ablation of atrial arrhythmias: state of the art," Lancet, vol. 380, pp. 1509-1519 (Oct. 27, 2012).
Levine et al., "Cardiotoxicity and serotonin syndrome complicating a milnacipran overdose," J. Medical Toxicology, vol. 7(4), pp. 312-316 (2011), abstract only.
Li et al., "Effects on Intramyocardial Injection of Platelet-rich Plasma on the Healing Process after Myocardial Infarction," Coronary Artery Disease, vol. 19, Issue 5, pp. 363-370, Aug. 2008.
Loder P.B. et al., The Effect of Collagen on Platelet Glycolysis and Nucleotide Metabolism, British Journal of Haematology, 1968, vol. 14, pp. 563-573.
Martinez-Gonzalez et al. "Do Ambulatory-Use Platelet-Rich Plasma (PRP) Concentrates Present Risks," Medicina Oral, vol. 7, pp. 375-390, 2002.
McCarthy, "New Surgical Options for the Failing Heart," J. of Heart Valve Disease, vol. 8(5), pp. 472-475 (1999).
Metcalfe et al., "Activation during preparation of therapeutic platelets affects deterioration during storage: a comparative flow cytometric study of different production methods," British J. Haematology, vol. 98, pp. 86-95 (1997).
Minamino et al., Endogenous Adenosine Inhibits P-Selectin-dependent Formation of Coronary Thromboemboli during Hypoperfusion in Dogs, Apr. 1998, J. Clin. Invest., vol. 101, No. 8, 1643-1653.
Nagae et al., "Intervertebral disc Regeneration Using Platelet-Rich Plasma and Biodegradable Gelatin Hydrogel Miscrosphere", Tissue Engineering 13 (1): 147-158 (2007).
Okuda, "Application of PRP (Platelet Rich Plasma) to Periodontal Treatment," Dental Outlook, vol. 98, No. 4, pp. 874-875, 2001 with English translation.
Palatianos, et al., Neutrophil Depletion Reduces Myocardial Reperfusion Morbidity, Annals of Thoracic Surgery, 2004, vol. 77, pp. 956-961.

(56) References Cited

OTHER PUBLICATIONS

Paques et al., "Effect of Autologous Platelet Concentrate in Surgery for Idiopathic Macular Hole", Ophthalmology 106 (5): 932-938 (1999).

Petrungaro, "Immediate Restoration of Multiple Tooth Implants for Aesthetic Implant Restorations", Implant Dentistry 11 (2) : 118-27 (2002).

Pruijt, et al., Neutrophils are Indispensable for Hematopoietic Stem Cell Mobilization Induced by Interleukin-8 in Mice, PNAS, Apr. 30, 2002, vol. 9, Issue 9, pp. 6228-6233.

Racz, et al., Buffy Coat or Platelet-rich Plasma?, Vox Sang, 1984, vol. 47, pp. 108-113.

Rashidi et al., Does Absolute Neutrophilia Predict Early Congestive Heart Failure After Acute Myocardial Infarction? A Cross-Sectional Study, Southern Medical Journal 101(1):19-23, Jan. 2008.

Roberts et al., "Relation between infarct size and ventricular arrhythmia," British Heart Journal, vol. 37, pp. 1169-1175 (1975).

Sawamura et al., "Characterization of In Vivo Effects of Platelet-Rich Plasma and Biodegradable Gelatin Hydrogel Microspheres on Degenerated Intervertebral Discs", Tissue engineering: Part A 15 (12): 3719-3727 (2009).

Sharpe, P.T., Chapter 5, Centrifugal Elutriation, R.H. Burdon and P.H. van Knippenberg editors, Laboratory Techniques in Biochemistry and Molecular Biology, Elsevier Science Publishers, Amsterdam, NL, pp. 91-94, 97-100, 101 and 105, 1998.

Shigenobu, "Effects of Platelet-Derived Growth Factor on Lacerated Tendons," Medical Magazine of Hiroshima University, vol. 48, No. 1, pp. 1-16, 2000.

Shim et al. "Stem Cell Cardiomyoplasty: State-of-the-Art," Annals of the Academy of Medicine, Singapore, vol. 33, No. 4, pp. 451-460, 2004.

Shvets, "Local Injections of Anesthetics and Corticosteroids in the Treatment of Degenerative Changes in the Spine," Chirugia narzadow ruchu i ortopedia polska, 45(3):259-63, 1980. (Abstract only.).

Snyder et al., "Calcium-Dependent Proteolysis of Actin During Storage of Platelet Concentrates," Blood, vol. 73, No. 5, pp. 1380-1385, 1989.

Tang, et al., "The Effects of pCO2 and pH on Platelet Shape Change and Aggregation for Human and Rabbit Platelet-Rich Plasma," Thrombosis Research, vol. 10, No. 1, pp. 135-146, 1977.

Taylor et al., "The Response of Rabbit Patellar Tendons After Autologous Blood Injection," Medicine & Science in Sports & Exercise, vol. 34, No. 1, pp. 70-73, 2002.

Valant, et al., Thrombotic Thrombocytopenic Purpura Plasma Enhances Platelet-Leucocyte Interaction In Vitro, British Journal of Haematology, 1998, vol. 100, pp. 24-32.

Valeri et al., Volume of RBCs, 24- and 48-hour posttransfusion survivals and lifespan of 51 Cr and biotin-X-N-hydroxysuccinimide (NHS)-labeled autologous baboon RBCs: effect of the anticoagulant and blood pH on 51 Cr and biotin-X-NHS elution in vivo, Transfusion, 2002, vol. 42, pp. 343-348.

Vassallo et al., "A Critical Comparison of Platelet Preparation Methods," Current Opinion in Hematology, vol. 13, pp. 323-330, 2006.

Wang, P.J., Circulation, 2006, vol. 113, p. 2374-2376.

Weibrich et al., "The Harvest Smart 1-3 PReP™ system versus the Friadent-Schütze platelet-rich plasma kit," Clinical Oral Implants Research, vol. 14 (2), pp. 233-239 (Apr. 2003).

www.mahasbtc.aarogya.com/blood-bank/preservation-and-storage, p. 2 only, accessed May 16, 2012.

Yang et al., "Dielectric Properties of Human Leukocyte Subpopulations Determined by Electrorotation as a Cell Separation Criterion," Biophysical Journal, vol. 76, pp. 3307-3314, Jun. 1999.

Yu et al., "A role for T lymphocytes in mediating cardiac diastolic function", Amer J Physiol Heart Circ Physiol, 2005, vol. 289, pp. H643-H651.

Zhang et al., "Emergent cardiopulmonary bypass in canines with penetrating cardiac wounds caused by gunshot," Emergency Medical J., vol. 24, pp. 764-768 (2007).

Ehrenfest, et al. "Classification of Platelet Concentrates: from Pure Platelet-rich Plasma (P-PRP) to Leucocyte- and Platelet-rich Fibrin (L-PRF)," Trends in Biotechnology, vol. 27, No. 3, pp. 158-167, 2008.

Gallo et al., "Effect of autologous platelet-rich plasma on heart infarction in sheep," Arch Cardiol Mex., vol. 83(3), pp. 154-158 (Jul.-Sep. 2013).

LaPlante et al., "Mechanisms of wound reepithelialization: hints from a tissue-engineered reconstructed skin to long-standing questions," The FASEB Journal, vol. 15, pp. 2377-2389 (Nov. 2001).

Rink, "Cytosolic Calcium in Platelet Activation," Cellular and Molecular Life Sciences, vol. 44, No. 2, pp. 97-100, downloaded from http://www.springerlink.com/content/j41h051h8866m352/?target=print, Abstract only, Feb. 1988.

Snyder et al., "Topical platelet growth factor therapy: of lotions and potions," Transfusion, vol. 41, pp. 1186-1189 (Oct. 2001).

Yu et al., "Effects of myocardial platelet rich plasma injection on rats with acute myocardial infarction:(99)Tc(m)-MIBI gated SPECT imaging evaluation results," Chin J Cardiol, vol. 40(5), pp. 392-396 (May 2012).

Zimmermann et al., "Different preparation methods to obtain platelet components as a source of growth factors for local application," Transfusion, vol. 41, pp. 1217-1224 (Oct. 2001).

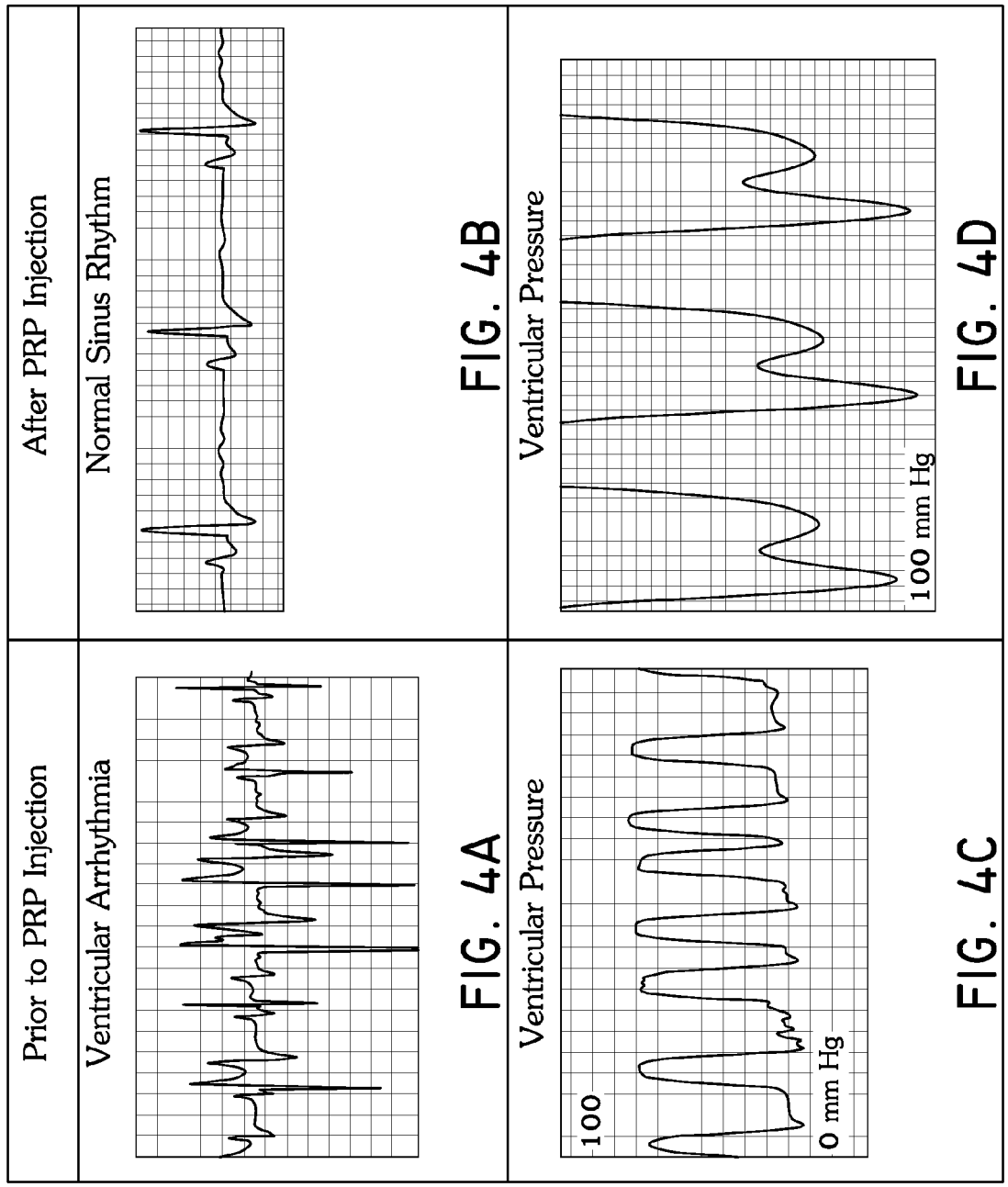

USE OF PLATELET RICH PLASMA COMPOSITION IN THE TREATMENT OF CARDIAC CONDUCTION ABNORMALITIES

RELATED APPLICATIONS

This application is a divisional of U.S. application Ser. No. 12/575,314 filed Oct. 7, 2009 which claims priority to U.S. Provisional Application No. 61/103,464, filed Oct. 7, 2008. Both applications are incorporated herein by reference.

BACKGROUND OF THE INVENTION

1. Field of the Invention

This invention relates generally to treatment of cardiac conditions and more specifically to treatment of a cardiac conduction abnormality (e.g., arrhythmia) using a composition comprising platelet rich plasma.

2. Description of the Related Art

Arrhythmias are a common disorder where the regular electric pacemaker activity of the heart may be disturbed. The disturbance may be caused by a blockage, delay, or misfiring of the electrical conduction system of the heart that controls the contraction and relaxation of the cardiac muscle. Arrhythmias may vary in severity, from asymptomatic disease to sudden cardiac death, and may lead to heart disease and stroke. According to the American Heart Association, about 2.2 million Americans suffer from atrial fibrillation, one type of arrhythmia.

To maintain regular, rhythmic beating, the heart comprises an electrical conduction system that controls the contraction of the cardiac muscle. FIG. 1 is a depiction of the electrical conduction system of a heart (100). In a normal rhythm, an impulse begins in the sino-atrial (SA) node (102) and is ultimately propagated to the myocardium to maintain blood flow through the heart. The SA node (102) is located adjacent to the right atrium (RA) and initiates an impulse. The impulse is then propagated to the left atrium (LA) via the intra-atrial pathway (104) and via the internodal pathways (106) to the atrioventricular (AV) node (108). This first propagation causes the atria to contract so that the blood flows from the atria into the ventricles. After a delay at the AV node (108), the impulse propagates to the left ventricle (LV) and the right ventricle (RV) through the Bundle of His (110) to the left bundle branches (112) and the right bundle branches (114). The ventricles contract when the impulse reaches the Purkinje fibers (116). In a medical setting, this sequence may be measured in an electrocardiogram (ECG or EKG) that records the electrical activity of the heart over time and may be recognized as a PQRST-wave.

Any disturbance in the electrical conduction of the heart may be typically considered to be an arrhythmia. Arrhythmias may be acute, chronic, and/or a combination of various arrhythmias. Disturbances in electrical conduction may classified by rate, mechanism, and/or site of origin. The mechanisms that may cause an arrhythmia include, for example, pre-excitation (e.g. from a bypass tract), automaticity, reentry, and triggered activity. The site of origin of the arrhythmia may be anywhere in the electrical conduction system and may be, for example, atrial, junctional, atrio-ventricular, and/or ventricular.

Arrhythmias may result in irregular rhythms, reduced heart rates (bradycardia), accelerated heart rates (tachycardia), or desynchronized heart muscle contractions which may reduce the mechanical function of the heart. For example, atrio-ventricular dyssynchrony, may cause the loss of the "atrial kick" which facilitates ventricular filling, or result in an atrium contracting against a closed atrio-ventricular valve. Ventricular dyssynchrony, where the left and right ventricles contract at different times, may reduce contractile efficiency when one ventricle is contracting while the other ventricle is relaxed, and may result in interventricular septal displacement that reduces the net forward blood flow of the ventricle. In still another example, atrial fibrillation results in a disorganized quivering of the atrial muscle and a loss of forward flow, which may predispose the patient to blood clot formation and a higher risk of stroke.

Arrhythmias may be treated in several ways, including, for example, physical maneuvers, anti-arrhythmic agents, other drugs, electrical pacing, radiofrequency ablation, and/or cryo-cautery. The treatment is typically selected based on a diagnosis that identifies the rate, site, and/or mechanism of the arrhythmia(s) to be treated. While some treatments may relieve some arrhythmias, the same treatments may aggravate or have no effect on other arrhythmias. For example, a physical maneuver such as a Valsalva maneuver or carotid sinus massage may be used to treat a superventricular tachycardia, but may not affect a ventricular tachycardia or a bradycardia.

Drug treatments that may be used to treat arrhythmias may have undesirable side effects and/or may be required for months if not years in order to maintain a regular heart rate. Indeed, some anti-arrhythmic agents even predispose a patient to an increased risk of certain arrhythmias. Hemodynamically unstable patients suffering an acute arrhythmia may be treated with electrical shocks using an automatic external defibrillator (AED) or manual defibrillator, but electrical shocks are not always successful in ending an arrhythmia and may cause significant discomfort or even burn the skin. Patients with a chronic arrhythmia may be treated with implantable cardiac rhythm management devices such as a pacemaker and/or defibrillator. However, these devices are subject to malfunction and may be difficult to implant in certain patients. Ablation of abnormal conduction pathways, or the formation of scar tissue to control the propagation of electrical activity, such as the Maze procedure used for atrial fibrillation, also requires invasive procedures and may only be effective in treating a narrow range of arrhythmias and while also increasing the patient's arrhythmia risk during the procedure or surgery.

As such, additional treatments for arrhythmias are desirable. Kits for treating arrhythmias are also desirable.

SUMMARY

Methods for treating cardiac conduction abnormalities (e.g., arrhythmias) are provided. Generally, the methods may include identifying a patient with a cardiac arrhythmia or an arrhythmia risk and delivering a platelet rich plasma (PRP) composition comprising PRP to treat the cardiac conduction abnormality. The cardiac conduction abnormality may be determined based on an abnormal heart beat, an electrocardiogram (ECG), electrophysiology study or by any other suitable mechanism. The functional effect of the conduction abnormality may also be assessed using electrocardiography, echocardiography, cardiac catheterization, cardiac magnetic resonance imaging, or cardiac nuclear medicine imaging. The cardiac abnormality or a heightened risk of a cardiac abnormality may be documented in, for example, a medical history, test results, patient file, procedure log, or other electronic or paper record. The PRP composition may be delivered to cardiac tissue in an amount sufficient to treat the conduction abnormality. For example, the amount may be about one to about three cubic centimeters, about three to about five cubic centimeters, about five to about seven cubic centimeters, or seven or more cubic centimeters. The PRP composition may comprise a platelet rich plasma, a buffering agent, and/or an anti-arrhythmic agent. In some examples, the PRP composition may be injected into the heart muscle or infused into one or more regions of the cardiac vasculature. The injection or infusion may be performed in a translumenal access procedure, a thoracoscopic procedure, an open chest procedure or any other access procedure.

The cardiac conduction abnormality may be associated with any of a variety of cardiac arrhythmias or arrhythmia risks. In some variations, the arrhythmia may be a bradycardia or a tachycardia, such as a ventricular tachycardia, for example. The arrhythmia may be caused at least in part by triggered activity, pre-excitation, automaticity, reentry, or by another mechanism, or a combination of mechanisms. The arrhythmia may be chronic, acute, or episodic. The arrhythmia may be diagnosed using an electrocardiogram generated by an electrocardiograph, a Holter monitor, or a cardiac event monitor.

In some variations, the PRP composition may be prepared from whole blood of the patient. The whole blood may be drawn prior to the arrhythmia or during the conduction abnormality. The PRP composition may be buffered to any suitable pH. In some examples, the suitable pH may be a physiological pH between about 7.3 and about 7.5.

The PRP composition may be delivered using any suitable medical procedure. For example, the PRP may be delivered using a minimally invasive procedure or an open or limited access surgical procedure. For example, a PRP composition may be delivered to, or adjacent to, a sino-atrial (SA) node, an atrio-ventricular (AV) node, Purkinje fibers, or another suitable region of the heart using a catheter configured to inject the PRP composition directly into the tissue, or configured to selectively infuse branches of the cardiac vasculature perfusing the tissue corresponding to the conduction system target site (or ischemic area of the myocardium). Systemic treatment with PRP is also contemplated, including peripheral infusion as well as an inhalable PRP composition.

The PRP composition may be used to treat a patient who may be presently exhibiting an arrhythmia, or a patient with an intermittent arrhythmia or at-risk of an arrhythmia but without overt rate or conduction disturbance at the time of PRP treatment. For example, a patient with Wolff-Parkinson-White syndrome may be treated using the PRP composition even if the heart is not tachycardic at the time of treatment. Further, the PRP composition may be administered at any suitable time during or following an acute arrhythmia. To illustrate, the PRP composition may be delivered within about one minute, about five minutes, about fifteen minutes, about thirty minutes, about one hour, several hours, days, or weeks following the acute arrhythmia.

The PRP composition may comprise PRP alone or PRP with one or more additional agents, and may be prepared in any suitable way. For example, the PRP composition may be prepared by adding an anti-arrhythmic agent to PRP. The anti-arrhythmic agent may be, but is not limited to, a sodium channel blocker, a beta blocker, a potassium channel blocker, a calcium channel blocker, or any other suitable anti-arrhythmic agent. The PRP composition may also comprise other suitable active agents such as anti-coagulants or clotting agents.

The methods may further comprise monitoring the cardiac conduction abnormality before, during, and/or after delivering the PRP composition. The monitoring may be initiated after the delivery by, for example, attaching a Holter monitor (or event monitor) to the patient.

Kits for treating the arrhythmia are also provided. The kits may include any suitable components. For example, a kit may comprise one or more preparation devices for preparing the PRP (e.g., a centrifuge) and one or more delivery devices configured to deliver a PRP composition to conduction tissue of a heart. The kit may also comprise one or more anti-arrhythmic agents.

The kits may further comprise one or more collection devices for collecting blood from a patient. The blood may be collected from a patient that has suffered or may be suffering from a cardiac conduction abnormality. In some embodiments, the blood may be collected from a patient who is suffering a myocardial infarction that may, in turn, increase the patient's risk of arrhythmia. The kit may additionally comprise instructions for using one or more of the kit components.

Embodiments of the invention are directed to methods of reducing conduction resistance to an electrical stimulation device designed to maintain cardiac rhythm by delivering a composition containing platelet rich plasma to an area of cardiac tissue, in which the electrical stimulation device is operably coupled to cardiac tissue.

BRIEF DESCRIPTION OF THE DRAWINGS

FIGS. 4A-4D show an electrocardiogram and ventricular pressure levels of a test subject before and after treatment of a reperfusion arrhythmia with PRP. FIG. 4A shows ventricular arrhythmia in a test subject prior to PRP injection. FIG. 4B shows normal sinus rhythm in a test subject after PRP injection. FIG. 4C shows ventricular pressure in a test subject prior to PRP injection. FIG. 4D shows ventricular pressure in a test subject after PRP injection.

DETAILED DESCRIPTION

Overview

Figure 1:
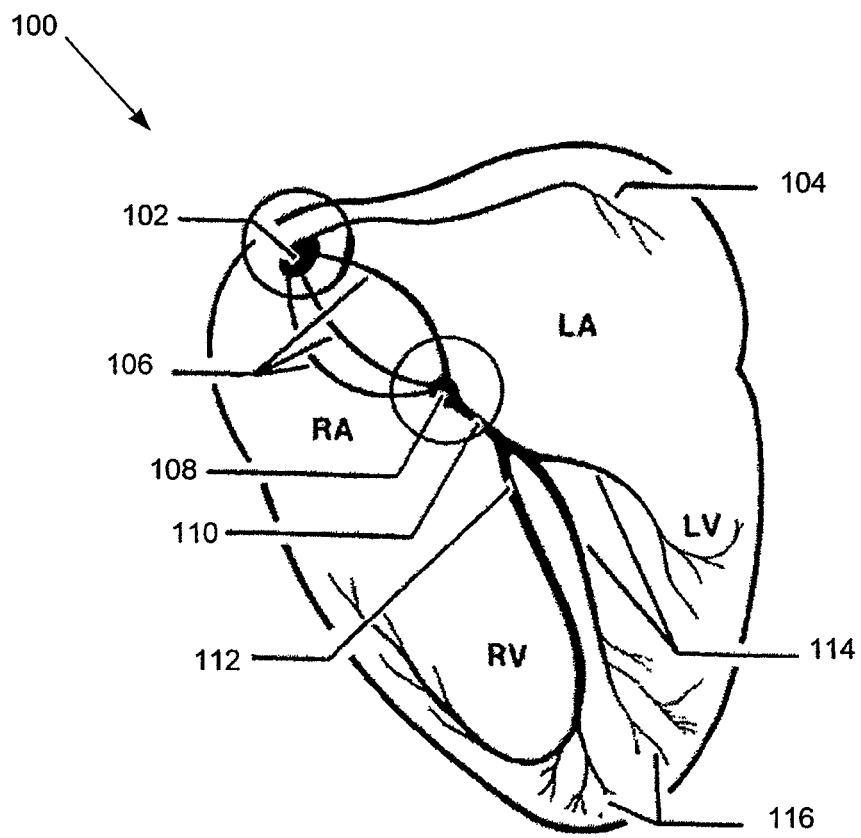
FIG. 1 is a schematic depiction of the electrical conduction system of a heart.

The term "arrhythmia" is used broadly herein to refer to cardiac abnormalities involving a disturbance in initialization and/or propagation of the impulses in a heart. As discussed above, the disturbance may be localized to a portion of the conduction tissues and/or may affect the entire electrical conduction system of the heart. There are several possible types of arrhythmias of varying severity.

As mentioned previously, an arrhythmia may be initially detected in a patient as an abnormally fast (i.e., tachycardia) or slow (i.e., bradycardia) heartbeat. Furthermore, some arrhythmias or conduction patterns may be characterized as regular, irregularly irregular (e.g., atrial fibrillation) or regularly irregular (e.g., Wenckebach or second degree heart block—type 1). The specific type of arrhythmia from which a patient may be suffering may be diagnosed based on an electrocardiogram (ECG or EKG). A normal electrocardiogram, as is known, depicts a PQRST-wave. The specific arrhythmia may be diagnosed based on one or more deviations from a normal PQRST-wave.

The term "PRP" as used herein is a broad term which is used in its ordinary sense and is a concentration of platelets greater than the peripheral blood concentration suspended in a solution of plasma. While normal platelet counts may range from about 140,000 to about 400,000 per microliter, some platelet concentrations of PRP may be in the range of about 500,000 to about 1,200,000 per cubic millimeter or more, and some platelet concentrations may be as low as 50,000 per cubic millimeter. PRP may be formed from whole blood, and may be obtained using autologous, allogenic, or pooled sources of platelets and/or plasma. PRP may be formed from a variety of animal sources, including human sources. In some examples, PRP may be further processed, including but not limited to leukoreduction and immunoadsorbtion. Other PRP compositions are further described in U.S. Pat. No. 6,811,777 to Mishra filed Apr. 11, 2003, which is hereby incorporated herein by reference in its entirety.

Various methods for delivering a PRP composition into conduction tissues of the heart to treat an arrhythmia are disclosed. In various embodiments, the composition may be delivered to the conduction tissues, the region of tissue directly adjacent to the conduction tissue, and/or healthy tissue. The PRP composition may comprise a platelet gel, or flowable material or liquid, other substances described herein, or any substance suitable for providing the desired level of treatment of the conduction tissues.

The PRP composition may be delivered to a patient in an emergency situation or as part of an elective procedure. For example, the PRP composition may be delivered in an emergency room to treat a ventricular tachycardia. In other instances, the PRP composition may be delivered weeks after an arrhythmia during an elective cardioversion.

In the treatment of cardiac conditions, the area known as "Koch's Triangle" (where a significant portion of the conduction tissues, including the AV node, is located) is typically avoided or treated with special care during cardiac surgery. Koch's Triangle is a portion of the right atrium defined generally by the coronary sinus, Todaro's tendon, the limbus ovalis, and the annulus of the tricuspid valve.

The PRP composition may be useful in treating arrhythmias that cause, or are caused by, a myocardial infarction. The myocardial infarction may be identified by determining whether enzymes such as cardiac troponin (e.g., troponin-I or T), creatine kinase (CK) including CK-MB, aspartate transminase (AST)/Glutamic Oxaloacetic Transaminase (GOT/SGOT)/aspartate aminotransferase (ASAT), lactate dehydrogenase (LDH), and/or myoglobin (Mb), and/or the like are present in the blood stream. The PRP compositions described herein may be delivered in the absence of the enzymes. Myocardial infarctions may be determined by identifying ST elevation in an ECG (e.g., during rest, a pharmacological stress test, and/or a physiological stress test), by coronary angiogram (e.g., noting acute closure of a vessel supplying myocardium at risk), by a nuclear medicine scan (e.g., technetium-99m or thalium-201), etc.

Further, according to some embodiments, the PRP composition may comprise PRP and one or more active agents. For example, the active agents may include anti-arrhythmic agents and/or anti-coagulants.

The compositions, devices, methods, and kits described herein are illustrative of various embodiments, variations, and adaptations. The disclosure is not intended to be limited to only the embodiments described.

Compositions

The PRP composition may comprise a PRP derived from a human or animal source of whole blood. The PRP may be prepared from an autologous source, an allogenic source, a single source, or a pooled source of platelets and/or plasma. To derive the PRP, whole blood may be collected, for example, using a blood collection syringe. The amount of blood collected may depend on a number of factors, including, for example, the amount of PRP desired, the health of the patient, the severity or type of the arrhythmia, the availability of prepared PRP, or any suitable combination of factors. Any suitable amount of blood may be collected. For example, about 20 cc to about 150 cc of blood may be drawn. More specifically, about 27 cc to about 110 cc or about 27 cc to about 55 cc of blood may be withdrawn. In some embodiments, the blood may be collected from a patient who may be presently suffering, or who has previously suffered from, a cardiac arrhythmia. PRP made from a patient's own blood may significantly reduce the risk of adverse reactions or infection.

The PRP may be prepared in any suitable way. For example, the PRP may be prepared from whole blood using a centrifuge. The whole blood may or may not be cooled after being collected. Isolation of platelets from whole blood depends upon the density difference between platelets and red blood cells. The platelets and white blood cells are concentrated in the layer (i.e., the "buffy coat") between the platelet depleted plasma (top layer) and red blood cells (bottom layer). For example, a bottom buoy and a top buoy may be used to trap the platelet-rich layer between the upper and lower phase. This platelet-rich layer may then be withdrawn using a syringe or pipette. Generally, at least 60% or at least 80% of the available platelets within the blood sample can be captured. These platelets may be resuspended in a volume that may be about 3% to about 20% or about 5% to about 10% of the sample volume.

In an exemplary embodiment, about 55 cc of blood may be withdrawn into a 60 cc syringe (or another suitable syringe) that contains about 5 cc of an anticoagulant, such as a citrate dextrose solution. The syringe may be attached to an apheresis needle, and primed with the anticoagulant. Blood (about 27 cc to about 55 cc) may be drawn from the patient using standard aseptic practice. In some embodiments, a local anesthetic such as anbesol, benzocaine, lidocaine, procaine, bupivicaine, or any appropriate anesthetic known in the art may be used to anesthetize the insertion area.

In some examples, the blood may then be centrifuged using a gravitational platelet system, such as the Cell Factor Technologies GPS System® centrifuge. The blood-filled syringe containing between about 20 cc to about 150 cc of blood (e.g., about 55 cc of blood) and about 5 cc citrate dextrose may be slowly transferred to a disposable separation tube which may be loaded into a port on the GPS centrifuge. The sample may be capped and placed into the centrifuge. The centrifuge may be counterbalanced with about 60 cc sterile saline, placed into the opposite side of the centrifuge. Alternatively, if two samples are prepared, two GPS disposable tubes may be filled with equal amounts of blood and citrate dextrose. The samples may then be spun to separate platelets from blood and plasma. The samples may be spun at about 2000 rpm to about 5000 rpm for about 5 minutes to about 30 minutes. For example, centrifugation may be performed at 3200 rpm for extraction from a side of the separation tube and then isolated platelets may be suspended in about 3 cc to about 5 cc of plasma by agitation. The PRP may then be extracted from a side port using, for example, a 10 cc syringe. If about 55 cc of blood may be collected from a patient, about 5 cc of PRP may be obtained.

The PRP composition may be delivered to help facilitate proper conduction. For example, the PRP composition may excite, slow or stabilize conduction pathways or various foci in the heart, or facilitate development of conduction pathways. For example, in the case of a blocked AV node, the PRP composition may provide an auxiliary conduction pathway and/or allow the existing (blocked) pathway to heal. In contrast, if the conduction tissue is spontaneously firing, the PRP composition may facilitate non-conductive tissue growth that does not propagate errant impulses.

As the PRP composition comprises activated platelets, active agents within the platelets are released. These agents include, but are not limited to, cytokines (e.g., IL-1B, IL-6, TNF-A), chemokines (e.g., ENA-78 (CXCL5), IL-8 (CXCL8), MCP-3 (CCL7), MIP-1A (CCL3), NAP-2 (CXCL7), PF4 (CXCL4), RANTES (CCL5)), inflammatory mediators (e.g., PGE2), and growth factors (e.g., Angiopoitin-1, bFGF, EGF, FGF, HGF, IGF-I, IGF-II, PDAF, PDEGF, PDGF AA and BB, TGF-.beta. 1, 2, and 3, and VEGF).

The PRP composition may be delivered as a liquid, a solid, a semi-solid (ex., a gel), an inhalable powder, or some combination thereof. When the PRP is delivered as a liquid, it may comprise a solution, an emulsion, a suspension, etc. A PRP semi-solid or gel may be prepared by adding a clotting agent (e.g., thrombin) to the PRP. The gel may be more viscous than a solution and therefore may better preserve its position once it is delivered to target tissue. Further, the PRP may be dried to form an inhalable powder.

In some instances, it may be desirable to deliver the PRP composition as a liquid and have it gel or harden in situ. For example, the PRP compositions may include, for example, collagen, cyanoacrylate, adhesives that cure upon injection into tissue, liquids that solidify or gel after injection into tissue, suture material, agar, gelatin, light-activated dental composite, other dental composites, silk-elastin polymers, Matrigel® gelatinous protein mixture (BD Biosciences), hydrogels and/or other suitable biopolymers. Alternatively, the above mentioned agents need not form part of the PRP mixture. For example, the above mentioned agents may be delivered to the target tissue after the PRP has been delivered to the target tissue to cause the PRP to gel. In some embodiments, the PRP composition may harden or gel in response to one or more environmental or chemical factors such as temperature, pH, proteins, etc.

The PRP may be buffered using an alkaline buffering agent to a physiological pH. The buffering agent may be a biocompatible buffer such as HEPES, TRIS, monobasic phosphate, monobasic bicarbonate, or any suitable combination thereof that may be capable of adjusting the PRP to physiological pH between about 6.5 and about 8.0. In certain embodiments, the physiological pH may be from about 7.3 to about 7.5, and may be about 7.4. For example, the buffering agent may be an 8.4% sodium bicarbonate solution. In these embodiments, for each cc of PRP isolated from whole blood, 0.05 cc of 8.4% sodium bicarbonate may be added. In some embodiments, the syringe may be gently shaken to mix the PRP and bicarbonate.

As noted above, the PRP composition may comprise one or more additional agents, diluents, solvents, or other ingredients. Examples of the additional agents include, but are not limited to, thrombin, epinephrine, collagen, calcium salts, pH adjusting agents, materials to promote degranulation or preserve platelets, additional growth factors or growth factor inhibitors, NSAIDS, steroids, anti-infective agents, and mixtures and combinations of the foregoing. In some variations, the PRP composition comprises one or more anti-arrhythmic agents.

Generally, anti-arrhythmic agents may be classified using the Vaughan Williams classification. In the Vaughan Williams classification, Class I drugs operate by interfering with the sodium (Na+) channel and include, for example, quinidine, procainamide, disopyramide, lidocaine, phenyloin, mexiletine, tocamide, encamide, flecainide, indecamide, propafenone, and moricizine. Class II agents are beta blockers and include, for example, propranolol, esmolol, timolol, metoprolol, sotalol, and atenolol. Class III agents affect potassium (K+) efflux and include bretylium, amiodarone, sotalol, ibutilide, and dofetilide. Class IV agents affect calcium channels and the AV node and include, for example, verapamil and diltiazem. Class V agents work by other or unknown mechanisms and include, for example, moricizine, digoxin, and adenosine. Any suitable anti-arrhythmic drug and/or combination thereof may be added to the PRP composition. The specific formulation used may be determined based on, for example, the type of arrhythmia, patient history, drug interactions, or any other suitable factor.

Furthermore, the PRP compositions may comprise a contrast agent for detection by an imaging technique such as X-rays, magnetic resonance imaging (MRI), or ultrasound. Examples of such contrast agents include, but are not limited to, X-ray contrast (e.g., IsoVue), MRI contrast (e.g., gadolinium), and ultrasound contrast.

In some embodiments, as discussed above, the anti-arrhythmic agent may be delivered to the patient mixed into the PRP composition. Additionally or alternatively, the anti-arrhythmic agents may be delivered separately to the electrical conduction system or other tissues of the heart. The anti-arrhythmic agent may be delivered via catheter prior to, simultaneously with, or subsequently to the PRP composition. Any suitable doses of the anti-arrhythmic agent may be delivered at any suitable intervals. Where one or more doses of an anti-arrhythmic agent or a combination thereof, the doses may be the same or may vary in terms of the agent selected and/or the amount of agent delivered. Some doses may include the PRP composition while others may not.

It should be understood that any suitable amount, mixture, and/or concentration of anti-arrhythmic agents may be added to the PRP. The timing, amount, mixture, and/or concentration of the PRP composition may be determined based on one or more patient characteristics, the type, and/or severity of the arrhythmia being treated, and/or any other suitable factor. The anti-arrhythmic agents may be delivered to the patient prior to, simultaneously with, and/or subsequently to delivery of the PRP. In some embodiments, one or more anti-arrhythmic agents may be mixed or otherwise combined with the PRP prior to delivery.

Devices and Methods

In some procedures, a PRP composition may be used as a non-specific arrhythmia treatment or arrhythmia prophylaxis. Thus, the specific type and/or location of the arrhythmia may or may not be identified prior to delivery of the PRP composition to the patient. For example, it may be enough to simply determine that the patient has suffered from, or is currently suffering from, an arrhythmia. Thus, an ECG is not always required in order to deliver the PRP. Of course, use of an ECG may be beneficial in certain circumstances. For example, the amount of PRP composition prepared and used may vary, based upon the type of arrhythmia. In some variations, whole blood is withdrawn prior to recording an ECG to begin preparation of the PRP composition. The ECG may then be used to determine an appropriate delivery mechanism simultaneously with the preparation of the PRP composition.

In some variations, the PRP composition is injected into a heart after the location, type, and severity of the arrhythmia (or some fraction thereof) has been identified. In certain instances, it may be helpful to identify one or more discrete locations within the heart to deliver the PRP composition in order to increase the likelihood that the treatment will be effective. For example, to treat an arrhythmia identified as an atrial fibrillation, it may be helpful to deliver the PRP composition to the SA node. Similarly, if the arrhythmia may be identified as a ventricular tachycardia, it may be desirable to deliver the PRP composition to the AV node.

The location of the conductive tissue dysfunction may be determined or approximated using various techniques. For example, in some variations, diagnostic procedures such as an electrophysiology study or an electrical mapping study of the heart may be used. In other variations, one or more imaging technologies such as MM, X-ray, CT scan, Positron Emission tomography (PET), Single Photon Emission Computed Tomography (SPECT), Electrical Impedance Tomography (EIT), Electrical Source Imaging (ESI), Magnetic Source Imaging (MSI), laser optical imaging and ultrasound techniques may be used. Other technologies and approaches that may be used include visual inspection during open chest surgical procedures, localized blood flow determinations, local electrical and structural activity, nuclear cardiology, echocardiography, echocardiographic stress test, coronary angiography, magnetic resonance imaging (MRI), computerized tomography (CT) scans, and ventriculography.

PRP compositions that are formulated as gels or other viscous fluids may be difficult to deliver via a needle or syringe. Thus, in variations where the use of a needle or syringe is desirable, it may be desirable to add a gelling and/or hardening agent to the PRP composition in situ. One or more needles or catheters may be configured to deliver the PRP composition and/or the agent simultaneously, or substantially simultaneously, to the cardiac tissue. For example, if a needle is used to deliver the PRP composition, the needle may comprise a plurality of lumens through which the PRP composition and the agent separately travel. Alternatively or additionally, separate needles may be used to deliver the components to the tissue at the same time or one after the other.

The PRP composition may be delivered minimally invasively and/or surgically. For example, the PRP composition may be delivered to the heart using a catheter inserted into the patient via the femoral vein or artery, the internal jugular vein or artery, or any other suitable vein or artery. The PRP composition may be delivered along with one or more medical devices, instruments, or agents to treat the arrhythmia and/or other cardiac conditions.

To deliver a PRP composition to the conduction system, a physician may use one of a variety of access techniques. These include surgical (e.g., sternotomy, thoracotomy, mini-thoracotomy, sub-xiphoidal) approaches, endoscopic approaches (e.g. intercostal and transxiphoidal) and percutaneous (e.g., transvascular, endocardial, and pericardial) approaches. Once access has been obtained, the composition may be delivered via epicardial, endocardial, or transvascular approaches. The composition may be delivered to the cardiac wall tissue or cardiac vessels in one or more locations. This includes intra-myocardial, sub-endocardial, and/or sub-epicardial administration.

Upon gaining access to the conduction tissues of the heart, the delivery device may be inserted through any appropriate vessel. The distal end of the delivery device may be then placed against the surface of the conduction tissues and one or more needles may be advanced into tissue. Following delivery of one or more components of the PRP composition, the needles, if any, may be retracted. The delivery device may then be repositioned for additional delivery of one or more components of the composition or may be removed from the patient. Incisions may then be closed using standard techniques.

In practice, the beating heart may be stabilized during the delivery of the PRP composition. For example, in some variations, the beating heart may be slowed or stopped by delivery of one or more drugs and/or by electrical stimulation of the heart. For example, a heart may be stabilized using pharmacologic asystole. Alternatively or additionally, a heart may be stabilized using pacing or other algorithms that render the heart fairly static. These procedures may initiate various cardiac states such as reversible initiation of asystole, fibrillation, or a prolonged refractory state. In still other embodiments, mechanical stabilization of the cardiac tissue may be achieved using any of a variety of mechanical stabilizing systems. In some examples, a combination of stabilizing procedures may be used.

The PRP composition may be delivered during a specific portion of the cardiac cycle, and in these variations, the use of one or more stimulation electrodes to act as a pacemaker during the delivery may be desirable. For example, the beat-to-beat period may be artificially lengthened so as to deliver the PRP composition during a specific phase of the cardiac cycle. In these variations, the delivery device may include one or more stimulation and/or sensing electrodes. For example, sensing electrodes may be used to sense contractions of the heart, thereby allowing the delivery of composition to be timed with cardiac contractions. It may be desirable to deliver one or more components of the PRP composition between contractions of the heart.

In some examples, one or more cardiac sensors may be used during the treatment procedures. The sensors may be any suitable sensor system (e.g., an electrical sensor, a chemical sensor, a pressure sensor, an intravascular imaging sensor, or a biosensor) capable of detecting one or more signals indicative of a cardiac contraction or heartbeat. A cardiac sensor may be used to monitor the electrical activity of the heart by picking up and amplifying electrical signals from the heart and displaying a visual output and/or providing an audio output. For example, the output may be displayed on a display interface. The physician may use this output to inject the needles and/or composition into the tissue at a specific point in the cardiac cycle. The cardiac sensor may be coupled to a cardiac stimulator to manipulate or control the cardiac rhythm.

In some variations, a nerve stimulator may be used to electrically manipulate cardiac rhythm by stimulating the vagus nerve. Vagal stimulation may produce asystole (slowing or stopping of the heart). Once the vagal stimulation is stopped, the heart may return to a normal rhythm. Alternatively, the heart may be paced. Vagal stimulation, alone or in combination with electrical pacing, may be used selectively and intermittently to allow a physician to perform delivery of one or more components of the composition into a temporarily stopped heart.

Typically, vagal stimulation may slow or even prevent the heart from contracting. Following initial slowing or stopping of the heart, one or more components of the PRP composition may be delivered to the heart. Following a brief interval of nerve stimulation while the delivery may be performed, nerve stimulation may be ceased and the heart may be allowed to contract. A cardiac stimulator or pacemaker may be used to cause the heart to contract or the heart may be free to beat on its own. In some variations, one or more electrodes may be used for pacing the heart as desired. A processor may control both cardiac and nerve stimulation. For example, a processor may cease nerve stimulation and automatically begin cardiac stimulation.

The delivery system may deliver the components of the PRP composition in a prescribed ratio (e.g., a ratio of the PRP to the anti-arrhythmic agent). The prescribed ratio may be calculated beforehand or determined on an ad hoc basis once delivery begins. To deliver the components in the prescribed ratio, the delivery device may include one or more gears having a corresponding gear ratio, one or more lumens having a proportional lumen size, or any other suitable mechanism. Some delivery devices may include one or more mixing chambers. The multiple components may be delivered using separate delivery devices or may be delivered one after the other using the same delivery device.

The delivery devices may be advanced through a vessel adjacent to the conduction tissues to be treated. The PRP composition may be injected directly into the conductive tissue using a needle and/or a needle-tip catheter. The PRP composition may alternatively or additionally be infused into the vessel.

When the PRP compositions are delivered using one or more catheters, any suitable catheter may be used. For example, the catheters may include one or more lumens and staggered or flush tips. The catheters may include needles or other devices (e.g., imaging devices) located at the distal end, and plungers or any other control located at the proximal end. The catheters and/or other delivery devices may have differently sized lumens to deliver multiple components of the PRP composition in the prescribed ratio. When catheters are used, a physician may navigate to the heart using one of the routes known for accessing the heart through the vasculature, including but not limited to navigation to a heart chamber for epicardial, endocardial, and/or transvascular delivery of the PRP composition.

Endocardial delivery of the PRP composition may comprise accessing a treatment site, for example, in the left ventricle of a heart, using a delivery device advanced percutaneously in an anterograde approach through the superior vena cava or inferior vena cava into the right ventricle. The delivery device may be passed through the interatrial septum into the left atrium and then into the left ventricle to reach treatment site. Alternatively, the device may be advanced using a transseptal procedure, e.g., through the intraventricular septum into the left ventricle. In another embodiment, the PRP composition may be injected directly into the interventricular septum from the right ventricle. An alternative endocardial delivery method may comprise accessing the treatment site using a delivery device advanced percutaneously in a retrograde approach through the aorta into the left atrium and then into the left ventricle.

Transvascular delivery of compositions may comprise passing the delivery device through the coronary sinus into the cardiac venous system via the cardiac veins and, if needed, leaving the veins by tracking through myocardial tissue. An alternative transvascular delivery method comprises accessing a treatment site through the aorta into a coronary artery to reach treatment site.

The devices for injecting or delivering the PRP compositions (catheter or otherwise) may include cooled parts or other temperature control mechanisms to keep the PRP composition at a desired temperature. Various embodiments of delivery devices may include a cooled chamber, and/or an agitator mechanism in a PRP chamber or injection chamber to prevent settling or clumping of the PRP components. For example, in some variations, the catheter or other delivery device has a cooled lumen or lumens for keeping the PRP composition cool during delivery. The delivery devices may additionally or alternatively include a mixing chamber for mixing the PRP composition prior to delivery. The PRP composition may also be stored in an agitating/vibrating chamber, or the physician may agitate the PRP composition once inside the delivery device by tilting or otherwise manipulating the device.

A practitioner may make multiple deliveries into various locations using a single device, make multiple deliveries into various locations using multiple devices, make a single delivery to a single location using a single device, or make a single delivery to a single location using multiple devices. The deliver devices may include at least one reusable needle or catheter. Some embodiments may include delivery devices having an automated dosing system (e.g., a syringe advancing system). The automated dosing system may allow each dose to be pre-determined and dialed in (may be variable or fixed). In some embodiments, an iontophoresis device may be used to deliver the PRP composition into the conductive tissue.

The PRP composition may alternatively or additionally be coated on one or more devices such as, for example, sutures, stents, screws, and/or plates. Anti-arrhythmia devices, such as pacemaker leads and automatic defibrillators may also be coated, sprayed, or dipped into the PRP composition prior to, simultaneously with, or subsequently to implantation.

It may be desirable to deliver the PRP composition to the conduction tissues while avoiding coincidental delivery to other cardiac tissues or other locations adjacent to the heart. For example, the PRP composition may gel or harden upon delivery to prevent migration. In some variations, a balloon catheter may be placed in the coronary sinus and inflated during delivery until the PRP composition has solidified or at least partially immobilized. Other variations may include a pressure control system on the delivery device to prevent pressure-driven migration of the PRP composition. Backbleed may also be prevented by keeping the needle in place for several seconds (e.g., about 5 to about 30 seconds, or about 5 to about 120 seconds) following an injection.

Sensors may be used to direct the delivery device to a desired location and/or to deliver the PRP composition. For example, real-time recording of electrical activity (e.g., an ECG), pH, oxygenation, metabolites such as lactic acid, $CO_2$, or the like may be used. The sensors may be one or more electrical sensors, fiber optic sensors, chemical sensors, imaging sensors, structural sensors, and/or proximity sensors that measure conductance. The sensors may be incorporated into the delivery device or be separate from the delivery device. In some embodiments, the sensors may sense and/or monitor such things as needle insertion depth, blood gas, blood pressure or flow, hemocrit, light, temperature, vibration, voltage, electric current, power, and/or impedance. The sensors may include one or more imaging systems and may be coupled to any appropriate output device, for example, a LCD or CRT monitor which receives and displays information.

The total volume of the PRP composition delivered to the patient may be based on the size of the heart, the amount of the affected conductive tissue, and/or the desired outcome of the procedure. For example, the total volume of composition injected may be less than 15000 µL.

The number of delivery sites in the heart may be based on the type and location of the arrhythmia(s), the desired location of the PRP composition, and the distance separating the desired locations. The number of delivery sites may range from about 1 to about 25 sites. The distance separating delivery sites may vary based on the desired volume of platelet gel to be delivered per delivery site, the desired total volume to be delivered, and/or the condition of the conductive tissue. At the delivery site, the PRP composition may be injected, infused, or otherwise disposed at or adjacent to the conductive tissue. The PRP composition may also be infused into the vasculature (i.e., vessels) upstream of the target site, so that it will flow towards the affected conduction tissue.

The location of the delivery sites may vary based on the size and shape of the affected conductive tissue, and the desired extent of the treatment of the tissue. For example, the PRP composition may be delivered into the affected conductive tissue, and/or into the tissue that bordering the affected conductive tissue. Similarly, the composition may be delivered to any combination of the regions of conductive tissue and other cardiac tissue.

Figure 2:
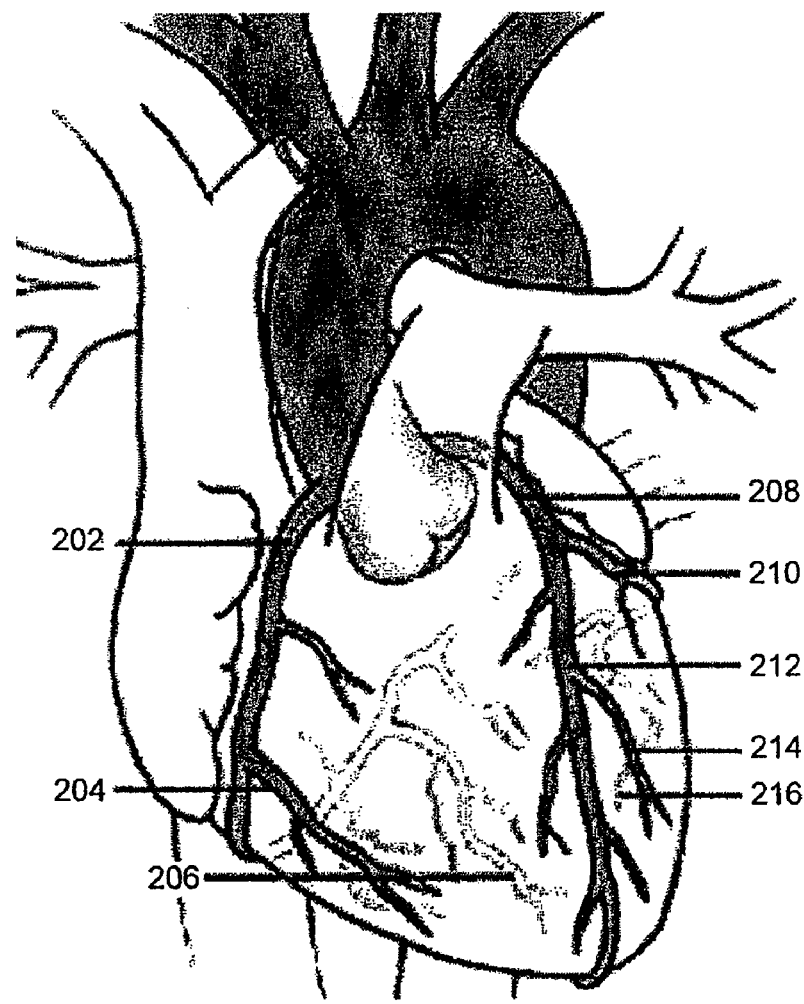
FIG. 2 is a schematic illustration of the cardiac vasculature.
Figure 3:
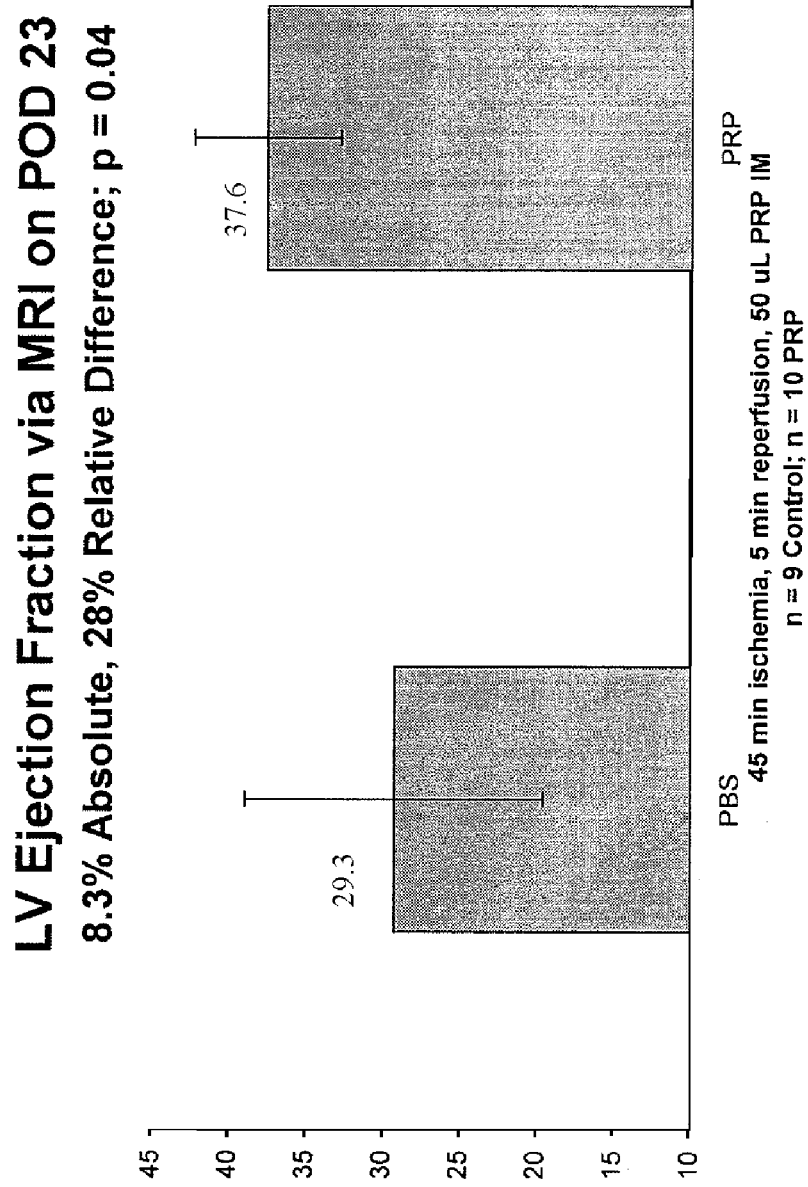
FIG. 3 shows Left Ventricle ejection fraction by MRI 3 weeks after heart attack in mouse ischemia-reperfusion model.

In some instances, selective infusion of a PRP composition may be less arrhythmogenic than needle injection of a PRP composition directly into the myocardium. FIG. 2 is a schematic illustration of the cardiac vasculature (200). The cardiac vasculature (200) comprises, for example, the right coronary artery (202), the acute marginal artery (204), the posterior descending artery (206), the left main coronary artery (208), the circumflex artery (210), the left anterior descending artery (212), the diagonal artery (214), and the obtuse artery (216). Certain arrhythmias may affect include aberrant pathways or foci that are perfused by certain branches of the cardiac vasculature. For example, branches of the right coronary artery (202) provide the blood supply to the AV node in about 90% of patients. Thus, selective access to the right coronary artery (202) may be used to treat abnormalities of the AV node. In another example, certain accessory tracts of Wolff-Parkinson-White syndrome affecting the upper ventricles may be treated by accessing the circumflex artery (210).

The timing of PRP delivery relative to an arrhythmic event may be based on the severity of the arrhythmia, the extent of the arrhythmia, the condition of the patient, and the progression of any concurrent arrhythmia treatments. The PRP composition may be delivered at any suitable time. For example, it may be delivered immediately after the onset of an arrhythmia, within one hour of an arrhythmia, one to eight hours following an arrhythmia, or three to four days after an arrhythmia after clinical stabilization of the patient when it is safer for the patient to undergo a separate procedure. The timing may be based upon the onset and/or the cessation of the arrhythmia. In some variations, the composition is delivered about one week, about 1 to about 3 weeks, about 1 to about 6 months, or even up to or more than about 1 year after the arrhythmia. Other times for injecting compositions into the conductive tissue are also contemplated, including prior to any anticipated arrhythmia, and immediately upon finding an area of conductive tissue responsible for one or more arrhythmias (for preventing additional arrhythmias). Of course, compositions may be injected into the conductive tissue years after an arrhythmia.

Alternatively or additionally, the PRP composition may be used prophylactically, e.g., with certain conditions associated with an increased arrhythmia risk or with episodic arrhythmias. For example, the PRP composition may be delivered one hour, thirty minutes, 15 minutes, 5 minutes, or just prior to or during a procedure associated with a heightened arrhythmia risk (e.g., a reperfusion procedure). To treat episodic arrhythmias, the PRP composition may be used after an episode, when an arrhythmia occurs, or before an arrhythmia is likely to occur.

In some variations, as discussed above, one or more anti-arrhythmic agents may be delivered to the patient mixed into the PRP composition. Additionally or alternatively, the anti-arrhythmic agents may be delivered separately to the electrical conduction system of the heart. The anti-arrhythmic agent may be delivered via catheter prior to, simultaneously with, or subsequently to the PRP composition. Any suitable doses of the anti-arrhythmic agent may be delivered at any suitable intervals. Where one or more doses of an anti-arrhythmic agent or a combination thereof, the doses may be the same or may vary in terms of the agent selected and/or the amount of agent delivered. Some doses may include the PRP composition while others may not.

In some embodiments, the PRP composition may be inhaled using, for example, an inhaler or a nebulizer. To deliver the PRP composition in powder form using, for example, an inhaler, the PRP composition may be dried once it may be prepared as described above according to known pharmaceutical techniques.

The devices and methods may be used in conjunction with current anti-arrhythmia therapies and/or concurrently with other medical procedures that are generally known to increase the likelihood of an arrhythmia. For example, and as discussed generally with respect to the methods and devices, various cardiac procedures may require slowing (bradycardia) and/or stopping (asystole) the heart for a period of time.

The PRP composition may be incorporated into an Advanced Cardiac Life Support (ACLS) protocol for treating acute cardiac arrhythmias. The ACLS protocol comprises one or more procedures for treating a patient based on a type of arrhythmia. The ACLS protocol comprises first establishing and securing an airway device (e.g., an Endotracheal Tube (ETT), Laryngeal Mask Airway (LMA), Cuffed Oropharyngeal Airway (COPA), Combitube, etc.) then ventilating with 100% oxygen gas and confirming the airway placement (e.g., exam, $ETCO_2$, and $SpO_2$). The rhythm and pulse may be evaluated. The medical personnel continues CPR, obtains IV access, and gives rhythm-appropriate medications according to specific algorithms based on the type, location, and severity of the arrhythmia.

In some instances, a cardioversion may be performed during ACLS or as an elective procedure to treat an arrhythmia. A cardioversion is a brief electrical shock to the heart to shock the heart into a normal rhythm. The initial cardioversion may comprise three shocks that may be synchronized to the arrhythmic heart beat. The shocks may be performed in increasing energy levels. For example, the first shock may be at 100 Joules, the second shock may be at 200 Joules, and the third shock may be at 300 Joules. The PRP composition may be delivered to the heart prior to, in between, and/or subsequently to the three shocks. In some instances, more than one dose of the PRP composition may be delivered during the cardioversion. In some embodiments (e.g., if the cardio version stabilizes the patient), whole blood may be withdrawn from the patient following the cardioversion for production of PRP composition to be delivered to the patient.

In the event of a ventricular tachycardia, a cardioversion may be performed, especially if the heart rate is greater than 150 beats per minute or where signs of hemodynamic instability are present. Before or after the cardioversion, the patient may also be treated using one or more anti-arrhythmic agents and/or PRP compositions. The anti-arrhythmic agent and/or the PRP composition may be selected based on the morphology of the tachycardia and/or the ejection fraction (EF) of the heart. For example, if the tachycardia is monomorphic and the EF is normal, arrhythmic agents such as procainamide and sotalol may be delivered. Alternatively, arrhythmic agents such as amiodarone and lidocaine may be administered. If, however, the EF is lower than normal, amiodarone or lidocaine may be administered over an IV and another cardioversion may be performed.

In instances where the ventricular tachycardia is polymorphic, the treatment may be selected based on the QT interval indicated by an ECG. If the QT is normal, the treatment selected may be depend on the EF of the heart. When the EF is normal, the anti-arrhythmic agent used may be a betablocker such as sotalol, and/or another agent including, but not limited to, lidocaine, amiodarone, and procainamide. When the EF is below normal, delivery of amiodarone or lidocaine may be synchronized with one or more cardioversion. If however, the QT interval is prolonged (i.e., torsades de pointes), the PRP composition may be delivered with and/or include magnesium, isoproterenol, phenyloin, and/or lidocaine. In some instances, the heart may be treated using overdrive pacing.

The PRP composition may also be delivered as disclosed herein during or after a bradycardia (i.e., slow heart beat). In these instances, the AV node may be blocking the impulse from propagating into the ventricles. To treat a bradycardia, atropine (e.g., 0.5-1.0 mg IV push q 3-5 min up to a maximum of 0.04 mg/kg), dopamine (e.g., 5-20 µg/kg/min), and/or epinephrine (e.g., 2-10 µg/min) may be administered. In these instances, transcutaneous pacing (TCP) may be performed if the bradycardia is severe.

In the event of atrial fibrillation or atrial flutter, the ACLS protocol comprises performing a cardioversion and administering one or more anticoagulants. The cardioversion may occur immediately or later as an elective cardioversion. Cardioversions may also be performed chemically using anti-arrhythmic drugs. In these embodiments, the PRP compositions may not include a clotting agent. Examples of anticoagulants may be selected based on ejection fraction (EF). If the patient has a normal EF, a calcium blocker or a beta blocker to control the heart rate may be administered. Some anti-arrhythmic agents that may be used include amiodarone, ibutilide, procainamide, flecainide, propafenone, and sotalol. If the patient has an EF of less than 40% and/or congestive heart failure (CHF), the heart rate may be controlled by administering digoxin, diltiazem, and/or amiodarone. In the case of Wolff-Parkinson-White syndrome characterized by a short PR interval and long QRS interval with a delta wave associated with paroxysmal tachycardia, amiodarone, procainamide, propafenone, sotalol, or flecainide may be administered.

In general, the ACLS protocol may be performed by alternating electrical shocks with administration of drugs while monitoring the heart rate using an ECG. The PRP composition may generally be administered with one or more other anti-arrhythmia and/or anti-coagulant drugs. A pre-prepared PRP may be used in emergency situations while an autologous PRP may be used after the patient is stabilized, for example, in conjunction with an elective cardioversion.

The PRP composition may also be used in an electrophysiology study (e.g., a cardiac electrical mapping study, with or without an ablation treatment) where the conduction system may be evaluated for abnormal conduction pathways or foci, and where portions of conductive tissue may be ablated to treat the abnormal impulse propagation. Ablation may be used, for example, in patients with Wolff-Parkinson-White syndrome or any of a variety of other arrhythmias, including those caused by reentry or automaticity, for example. The electrophysiology study may be used to determine the pathological conduction pathways and to ablate them. The PRP may be delivered before, during, and/or after the electrophysiology study to stabilize or otherwise treat the aberrant pathways.

In some variations, as briefly described above, the PRP composition may be used in conjunction with a procedure to deliver one or more implants to the heart. Some of these procedures may be associated with acute risks of arrhythmia or exacerbate existing arrhythmias. The implants may be devices for treating a chronic arrhythmia or to treat other medical conditions. Examples of implant procedures include implantation and/or removal of pacemakers and automatic defibrillator leads. The PRP composition may be delivered prior to, simultaneously with, and/or subsequently to, the placement of leads in the conduction tissues of the heart. In one example, a patient undergoing implantation of a cardiac rhythm management device may be pre-treated with a PRP composition about from about 1 to about 4 hours or more before the procedure, sometimes about 1 to about 2 days before, and other times about 1 week or more before. The PRP composition may have an additional desirable effect by promoting fibrous tissue growth to anchor the leads. In some variations, the leads, devices, or other implants (e.g., sutures) are coated with the PRP composition.

The PRP composition may be delivered at any suitable dose. In some embodiments, the dose may be between about 1 cc and about 3 cc, between about 3 cc and about 5 cc, between about 5 cc and about 10 cc, between about 10 cc and about 20 cc, or more. The dose may be delivered according to a medical procedure (e.g., at specific points in a procedure) and/or according to a schedule. For example, prior to an elective cardioversion, the PRP composition may be delivered about 24 hours, about 12 hours, about 6 hours, about 2 hours, and/or about 1 hour before the procedure begins. A portion of the dose and/or an additional dose may be delivered during the elective cardioversion (e.g., immediately before the initial shock, between shocks, and/or immediately after the final shock). One or more doses of the PRP composition may be delivered after the elective cardioversion and/or on an as needed basis.

As mentioned previously, a PRP composition may additionally or alternatively be used to prevent and/or treat arrhythmias that may occur during other cardiac procedures. Cardiac procedures may include anti-arrhythmia procedures, procedures to correct congenital heart defects, or other pathologies. Examples of other cardiac procedures include, but are not limited to, angioplasty, coronary artery bypass, Minimally Invasive Direct Coronary Artery Bypass (MIDCAB), off-pump coronary artery bypass, Totally Endoscopic Coronary Artery Bypass (TECAB), aortic valve repair, aortic valve replacement, mitral valve repair, mitral valve replacement, Ross procedure, Bentall procedure, pulmonary thromboendarterectomy, valve-sparing aortic root replacement, cardiomyoplasty, Dor procedure, heart transplantation, septal myectomy, ventricular reduction, pericardiocentesis, pericardiectomy, atrial septostomy, Blalock-Taussig shunt procedure, Fontan procedure, Norwood procedure, Rastelli procedure, Maze procedure (Cox maze and minimaze), and/or pacemaker insertion. The PRP composition may used to prevent an arrhythmia associated with reperfusion of the cardiac tissue during any of the above procedures. As is known, reperfusion may cause a spontaneous arrhythmia to occur after cardiac surgery.

In some embodiments, the PRP composition may be delivered to prevent and/or treat an arrhythmia resulting from an electrolyte imbalance caused by, for example, kidney failure. In kidney failure, electrolyte levels essential to the proper running of cardiac conduction system (e.g., calcium, potassium, sodium, magnesium, etc.) may be improperly managed. The resulting electrolyte balance may prevent the conduction tissues from propagating the impulse normally.

The PRP composition may also be used in the placement of a single lumen pulmonary artery catheter or a Swan-Ganz catheter. The Swan-Ganz catheter may be advanced through the superior vena cava to the pulmonary artery. Because the Swan-Ganz catheter passes through the right atrium and the right ventricle, where Koch's Triangle is located, there is a heightened risk of arrhythmia. To prevent or treat an arrhythmia, the PRP may be delivered prior to, simultaneously with, and/or subsequently to, the placement of the Swan-Ganz catheter. In some embodiments, the Swan-Ganz catheter may be coated with the PRP. The PRP composition may also be delivered periodically while the Swan-Ganz catheter is in place.

In some embodiments, the PRP composition may be delivered to the patient based on the mechanism of the arrhythmia. As discussed herein, an arrhythmia may be caused by one or more mechanisms including automaticity, triggered activity, pre-excitation and/or re-entry. These mechanisms may correspond to one or more cardiac pathologies aside from the arrhythmia itself.

An arrhythmia may be caused at least in part by abnormalities in automaticity, i.e., an abnormal spontaneous polarization, of the cardiac tissues. Automaticity normally originates in the SA node and propagates through the rest of the conduction system. However, abnormalities may cause a portion of the conduction tissues to depolarize out of sync with the rest of the conduction system. Automaticity may arise, for example, when the conduction of the impulse from the SA node is blocked.

Triggered activity typically occurs when the ion channels in individual heart cells are damaged, blocked, or otherwise altered resulting in abnormal propagation of the impulse. In some instances, triggered activity can lead to sustained abnormal rhythm and may be a result of anti-arrhythmic drugs.

Pre-excitation can occur when accessory or bypass tracts provide alternate conduction pathways for myocardial depolarization. For example, these accessory or bypass tracts may bypass the AV node, resulting in premature depolarization of the ventricular muscle. In some instances, the premature depolarization wave may merge with the depolarization wave from the normal conduction pathway, resulting in a fusion beat or wave.

Re-entry is another possible mechanism that may be used to characterize an arrhythmia. Typically, the impulse is conducted through the conduction system in a uniform fashion from the SA node to the AV node to the Purkinje fibers to depolarize each in turn. However, if a portion of the conduction tissue is too slow or too quick to depolarize, the conduction tissues that normally depolarize in response may depolarize more than once in a single cardiac cycle. For example, the conduction tissues may depolarize first in response to the original impulse and then quickly depolarize again in response to the delayed impulse. Re-entry is associated with several types of arrhythmias including, for example, atrial flutter, supraventricular tachycardia, ventricular tachycardia and fibrillation arrhythmias.

In some examples, a PRP composition may be used to treat a patient diagnosed with an acute myocardial infarction. Treatment with the PRP composition may occur in the field or in the emergency room setting. Criteria for PRP composition treatment may include positive cardiac markers, ST-elevations, or new wall motion abnormalities identified on echocardiogram, for example. The decision to treat with a PRP composition, and the treatment location(s), may depend upon one or more characteristics of the myocardial infarction. For example, a myocardial infarction may be characterized as a ST-elevation myocardial infarction (STEMI) or non-ST-elevation myocardial infarction (NSTEMI), a Q-wave or non-Q-wave myocardial infarction, and whether they are subendocardial or transmural. Myocardial infarctions may also be characterized anatomically by cardiac wall region and/or the suspected blockage site in the cardiac vasculature. Myocardial infarctions may also be characterized as anterior, lateral, inferior, posterior, septal, or right-ventricular in location, and may involve disease or blockage of the left-anterior descending, left circumflex, left main, posterior-descending and right coronary arteries, for example.

In other examples, timing of the PRP composition treatment may be based upon other treatments that are indicated in a patient with a myocardial infarction. In some instances, a PRP composition may be delivered before, during, and/or after reperfusion therapy is performed to treat an acute myocardial infarction or a previous myocardial infarction. Reperfusion therapies may include thrombolytic therapy, angioplasty, stenting (including bare metal stents and drug-eluting stents) or coronary artery bypass graft (CABG) surgery. In some instances, reperfusion therapy may be associated with an increased risk of an arrhythmia, including sudden death. Also, it is believed that the etiology of reperfusion arrhythmias or reperfusion arrhythmia risk may be different from the arrhythmia etiologies associated with the myocardial infarction itself. For example, some reperfusion arrhythmias may be caused by triggered activity and/or re-entry. A PRP composition may be prepared before or at the start of a reperfusion procedure, but not used unless an arrhythmia occurs during the procedure. In other reperfusion procedures, the patient may be prophylactically pre-treated with a PRP composition before reperfusion occurs, e.g., before guidewire passage across an occlusion, stent positioning, stent expansion, or reestablishment of coronary flow through a bypass segment.

Kits

Kits may include any device, component, or combination of devices and/or components described herein. For example, the kits may include one or more preparation devices, one or more delivery devices, one or more collection devices, and/or instructions for use. The one or more preparation devices may be for preparing PRP and may comprise a centrifuge, for example. The one or more delivery devices may be configured to deliver a PRP composition comprising the PRP to a region of the heart to treat a cardiac arrhythmia. The one or more collection devices may comprise one or more syringes, apheresis needles, or other devices for collecting blood from a patient. The patient may be presently suffering or have suffered a cardiac arrhythmia. The components of the kit may be packaged in sterile containers. The kits may comprise one or more single-use components. Instructions may be in written or pictograph form, or may be on recorded media including audio tape, audio CD, video tape, DVD, CD-ROM, or the like.

The kits may be designed to target specific cardiac arrhythmias. In one variation, a kit may be designed for use with a ventricular tachycardia. Such a kit may include, for example, one or more collection devices, ECG leads, and/or one or more anti-arrhythmic agents.

In addition to the foregoing uses for the compositions, methods and systems described herein, it will be apparent to those skilled in the art that other injured tissues, in addition to injured cardiac tissue, would benefit from the delivery of structural support materials to treat the injuries. Non-limiting examples of such tissues include the stomach, to reduce food intake and increase satiety; the abdominal wall, to prevent and treat hernias and the bladder to prevent or treat incontinence. Such tissues may additionally include vascular tissues.

EXAMPLES

Example 1

PRP was prepared using a centrifuge unit made by Harvest (Plymouth, Mass.). (Similar units are available as The Biomet GPS system, the Depuy Symphony machine and the Medtronic Magellan machine.) Approximately 55 cc of blood was drawn from the patient using a standard sterile syringe, combined with 5 cc of a citrate dextrose solution for anticoagulation, and then spun down to isolate the platelets according to the manufacturer's protocol. These platelets were then resuspended in approximately 3 cc of plasma. The resulting platelet rich plasma solution (PRP) was quite acidic and was neutralized with using approximately 0.05 cc of an 8.4% sodium bicarbonate buffer per cc of PRP under sterile conditions to approximately physiologic pH of 7.4. The PRP was not activated through addition of exogenous activators. This PRP composition is referred to herein as autologous platelet extract (APEX).

Example 2

Cardiac Muscle

Adult female mice (n=19) underwent left anterior descending (LAD) artery ligation (45 minutes) followed by 5 minutes reperfusion to mimic myocardial infarction. An APEX composition was prepared as described in Example 1 The extract was not activated through the addition of exogenous agent(s).

Unactivated PRP (n=10) or saline (n=9) was injected into murine myocardium. Three weeks later MRI was used to evaluate ejection fraction.

The data is shown in FIG. 1. PRP improves cardiac function by 28% (as measured by Left Ventricular Ejection Fraction) relative to control at 3 weeks after a heart attack. The data is statistically significant at p=0.04. This data supports the use of PRP in an ischemia-reperfusion heart model.

Example 3

Treatment of a Reperfusion Arrhythmia in an Animal Model

Arrhythmias frequently occur when ischemic cardiac tissue is reperfused with blood. This can occur in a variety of situations; however the most common is following an acute myocardial infarction. Typically, when blood flow is successfully reestablished after a coronary artery has been blocked, reperfusion arrhythmias can occur. These arrhythmias are usually in the form of ventricular ectopy including, but not limited to, non-sustained ventricular tachycardia, sustained ventricular tachycardia and ventricular fibrillation. These arrhythmias can result in hemodynamic compromise and, in some cases, death.

The successful test of PRP in an animal model simulating a reperfusion arrhythmia following an acute myocardial infarction was conducted as follows: In a 40 Kg swine, the left anterior descending artery was identified using coronary angiography and then occluded with an angioplasty balloon (thus mimicking a myocardial infarction). Hemodynamic and electrocardiographic measurements were recorded during the procedure. After sixty minutes of arterial blockage, the balloon was deflated resulting in reperfusion. This led to pronounced ventricular ectopy in the form of ventricular couplets, triplets, and non-sustained ventricular tachycardia.

Following 30 minutes of catheter-based endocardial ventricular mapping, ventricular arrhythmias persisted even without a catheter in place and continued while an injection catheter was placed into the left ventricle cavity. Platelet rich plasma (PRP) was then injected into myocardial region of the acute occlusion in an attempt to improve cardiac function. Five minutes after ten injections of 0.2 ml of PRP under fluoroscopic guidance, the cardiac rhythm returned to a normal sinus pattern without any ventricular ectopy.

FIGS. 4a and 4b depict EKG tracings taken of the test subject before and after treatment with the PRP. FIG. 4a, recorded prior to the PRP treatment, shows a highly irregular pattern consistent with multifocal premature ventricular contractions consistent with ischemia and recent reperfusion. The fact that the QRS complexes are of different shapes indicates that pacing is occurring from multiple sites in the myocardium in a disorganized manner and thus indicates a serious disruption in the heart's normal pacemaking. FIG. 4b shows an EKG taken following PRP treatment and shows that the rate and rhythm have normalized.

FIG. 4c shows a ventricular pressure measurement as measured using cardiac catheterization. The relatively low pressures show that the ventricles are unable to generate sufficient pressures to pump blood efficiently during the arrhythmia as they are contracting in an irregular and disorganized manner. By contrast, the pressures recorded under FIG. 4d are much higher. This reflects that the myocardium is able to fill and contract properly so as to function effectively.

Example 4

Treatment of Acute Coronary Syndrome with PRP

A patient presents with symptoms of myocardial ischemia such as chest pain. The diagnostic evaluation including a physical exam, EKG, as well as laboratory studies determines that the patient is having acute coronary syndrome such as unstable angina, Non-ST elevation myocardial infarction, or ST elevation myocardial infarction. A blood sample is drawn to create platelet rich plasma. The patient is taken to the catheterization laboratory to perform reperfusion therapy and then have platelet rich plasma applied, injected, or instilled to improve cardiac rhythm or protect against reperfusion arrhythmia. In another embodiment, the patient would go to the catheterization laboratory to have PRP either injected or instilled in a delayed manner to prevent future arrhythmia.

The PRP in the above example can be prepared using a variety of techniques including, but not limited to, centrifuges, gravity filtration devices, cell sorting or others. It can be combined with stem cells, genetic engineering or mechanical devices such as permanent or bioaborbable pacemaker or stent. The PRP can be autologous or made from allogenic sources. It can be made and then stored in a frozen or lyophilized state to be applied to the tissue later. In a preferred form it would be buffered to physiologic pH but it may also be valuable to instill PRP at either acidic or basic pH for specific clinical indications such as ablation of an abnormal conduction pathway. In yet another embodiment, the PRP could be prepared in a form that is depleted of neutrophils or other fractions of white blood cells either partially or completely.

Example 5

Treatment of Arrhythmia Using the PRP Formulation from Example 4

A patient presents with symptoms of palpitations, lightheadedness and pre-syncope or syncope. A diagnostic evaluation including physical exam and EKG determines that the patient is in a sustained or non-sustained arrhythmia such as, but not limited to, supraventricular or ventricular tachycardia. The patient is treated at the bedside or taken to the catheterization laboratory to have PRP injected or instilled into the location of the arrhythmia as located by topographic electrocardiogram or catheter-based electrophysiology study.

Example 6

Treatment of Reperfusion Arrhythmia Using the PRP Formulation from Example 4

PRP can be used to prevent arrhythmia associated with reperfusion in ischemic myocardial tissue. A patient who is undergoing cardiac surgery requiring bypass support such as, but not limited to, coronary artery bypass grafting, valve repair, valve replacement, cardiac transplantation, or other cardiac surgeries can have PRP injected or instilled into the myocardial tissue prior to, during, or after reperfusion. Reperfusion occurs when coming off the bypass machine. Injection is performed using needle injection under direct visualization or via a catheter placed into the heart under image guidance. The PRP is administered via single or multiple injections.

Example 7

Treatment of Bradycardia Using the PRP Formulation from Example 4

Bradycardias are usually the result of poor signal generation by cardiac pacing tissue or by abnormalities within conduction tissues. When the normal pacing system fails, the heart relies on various accessory pacemakers that beat at a slower rate than the SA node. This is often associated with increasing patient age as well as with histological evidence of fibrosis of the tissues involved. One such example is "sick sinus syndrome," a disorder that results in the development of significant bradycardia and the need for an implantable pacemaking device.

Patients with bradycardia can present with lightheadedness, near-syncope or full syncope. The diagnosis can be established using an EKG or a rhythm monitor. Once identified, early treatment to prevent further progression of the disease can result in avoiding the need for an implantable electrical pacemaker. Treatment with PRP reduces further fibrotic changes to the cardiac tissue and reduces local inflammation thus improving the generation of an impulse signal thus preventing the worsening of the bradycardia.

A patient presents with symptoms of syncope. History, physical examination and EKG result in a diagnosis of likely sick sinus syndrome. The patient then undergoes an electrophysiology study in the catheterization laboratory to "map" the electrical conduction of the SA node and the refractory period using a specialized catheter positioned in the right atrium under flourscopic visualization. Once identified, a second catheter with a small injection catheter on the tip is positioned on the same tissue as the signal sensor and platelet rich plasma injected into the location via an endomyocardial technique. Since this injection can result in temporary inability to produce a pacing signal from the SA node, the sensor catheter has the ability to pace the heart at a backup rate sufficient to support systemic hemodynamics. This procedure is performed once or multiple times to produce the desired effect of improving the patient's cardiac rhythm. Proof of improvement is measured via EKG or other diagnostic device or method.

Example 8

Treatment of a Patient with Heart Block Using the PRP Formulation from Example 4

A patient presents with symptoms of syncope. History, physical examination and EKG result in a diagnosis of a disruption in the cardiac conduction system at the level of the AV node ("heart block"). A subsequent electrophysiology study performed in the catheterization laboratory identifies the location of the disruption on the conduction system. While one monitor with pacing ability monitors the heart rate, a second catheter with a small injection catheter on the tip is positioned at the site of the conduction abnormality and platelet rich plasma is injected into the location via an endomyocardial technique one or more times. The resolution of the heart block is assessed via EKG or other diagnostic method.

Example 9

Treatment of Myocardial Tissue to Reduce Threshold and Increase Battery Life for Pacing Bradycardias are often treated by the placement of a permanent pacemaker. Such devices provide electrical stimulation of the myocardial conductive tissue using leads that are in contact with the epicardial or endocardial surface of the heart. "Myocardial capture" is achieved by delivering a capture signal capable of stimulating myocardial tissue. Myocardial fibrosis can necessitate higher pacing voltages to achieve capture. Damage to cardiac tissue from the pacemaker leads themselves can result in local fibrosis, thus necessitating higher pacing voltages and thereby reducing pacemaker battery life. Treatment with PRP can reduce the progression of fibrosis or even reduce existing fibrosis. This can minimize the energy consumption of the pacemaker and extend battery life.

A patient presents with symptomatic bradycardia that requires the placement of a permanent pacemaker (PPM). PRP is injected or instilled into the myocardial region wherein the pacemaking lead or patch is attached to the endocardial or epicardial surface. This is performed before, during or after the placement or attachment of the lead or patch. In one embodiment, an injection catheter is used to direct the injection of PRP into the region wherein the active fixation lead is to be attached. This can be performed in the catheterization laboratory under fluoroscopic guidance, with the endocardial injection occurring prior to, during or after the fixation of the lead. In an alternative embodiment, the patient is in the operating room for placement of a epicardial patch for pacing. The patient would have PRP injected or instilled into the location of the epicardial patch before, during or after the placement of the patch for pacing. In yet another embodiment, PRP is delivered via intramuscular injection or via a transdermal patch to enhance cardiac function or improve cardiac rhythm. In all of these embodiments the goal is to reduce fibrosis and enhance electrical conductivity. Treatment of myocardial tissue with PRP can facilitate functional pacing in the heart, reduce conduction resistance from fibrosis, and thereby reduce the energy requirements for the pacemaker and ultimately extend its battery life.

Example 10

Treatment of Myocardial Tissue to Reduce the Defibrillation Threshold and Energy Requirements of Defibrillation Devices Patients with various conditions including coronary artery disease, ischemic or non-ischemic cardiomyopathy or a history of ventricular arrhythmias can have an implantable cardiac debribrilator (ICD) placed to treat a life-threatening arrhythmia if and when they arise. Patients with cardiomyopathy often have myocardial fibrosis which increases resistance and necessitates a higher electrical charge to defibrillate the ventricle. PRP can be used to treat the fibrosis either prior to, during, or after the placement of an ICD. PRP can also be used in the treatment of patients undergoing heart transplant or valve surgery to improve rhythm or function.

A patient is diagnosed with ischemic cardiomyopathy and his doctors recommend that he have an ICD. Prior to ICD placement, the cardiac tissue in the area where the leads of the ICD are to be placed is injected or infused with PRP. Local fibrosis is reduced thus enabling the ICD to operate at a lower voltage when activated. This extends the battery life of the ICD.

While methods, devices, and kits have been described in some detail here by way of illustration and example, such illustration and example may be for purposes of clarity of understanding only. It will be readily apparent to those of ordinary skill in the art in light of the teachings herein that certain changes and modifications may be made thereto without departing from the spirit and scope of the appended claims.

What is claimed is:

1. A method for treating a cardiac conduction abnormality, comprising:
    identifying a cardiac conduction abnormality in a patient; and
    delivering a platelet rich plasma composition to the patient, wherein the platelet rich plasma composition is in an inhalable form.

2. The method of claim 1, wherein the conduction abnormality is a cardiac arrhythmia.

3. The method of claim 1, wherein the patient has a negative cardiac enzyme elevation.

4. The method of claim 1, further comprising monitoring the conduction abnormality after delivering the platelet rich plasma composition.

5. The method of claim 1, wherein the conduction abnormality is selected from the group consisting of bradycardia, tachycardia, ventricular tachycardia, and ventricular fibrillation.

6. The method of claim 1, wherein the conduction abnormality is chronic, acute or episodic.

7. The method of claim 1, wherein determining a cardiac conduction abnormality exists comprises using an electrocardiogram, Holter monitor or a cardiac event monitor.

8. The method of claim 1, wherein the platelet rich plasma composition is prepared from whole blood of the patient.

9. The method of claim 1, wherein the platelet rich plasma composition is buffered to a physiological pH, and wherein the physiological pH is between about 7.3 and about 7.5.

10. The method of claim 1, wherein the inhalable form is an inhalable powder.

11. The method of claim 1, wherein the treatment further comprises administering an anti-arrhythmic agent selected from the group consisting of a sodium channel blocker, a beta blocker, a potassium channel blocker, and a calcium channel blocker.

12. The method of claim 1, wherein the inhalable form is delivered with a nebulizer or inhaler.

13. The method of claim 1, wherein the conduction abnormality is due at least in part to reperfusion therapy.

* * * * *